(12) United States Patent
Ushakov

(10) Patent No.: US 10,067,359 B1
(45) Date of Patent: Sep. 4, 2018

(54) EYEGLASSES WITH A FIXED FRAME AND A ROTATABLE FRAME

(71) Applicant: Alexey Leonidovich Ushakov, Moscow (RU)

(72) Inventor: Alexey Leonidovich Ushakov, Moscow (RU)

( * ) Notice: Subject to any disclaimer, the term of this patent is extended or adjusted under 35 U.S.C. 154(b) by 0 days.

(21) Appl. No.: 15/688,968

(22) Filed: Aug. 29, 2017

(30) Foreign Application Priority Data

Jul. 5, 2017 (RU) .................................. 2017123756

(51) Int. Cl.
*G06C 9/00* (2006.01)
*G02C 7/08* (2006.01)
*G02C 9/02* (2006.01)
*G02C 7/16* (2006.01)

(52) U.S. Cl.
CPC ............... *G02C 7/086* (2013.01); *G02C 7/16* (2013.01); *G02C 9/02* (2013.01)

(58) Field of Classification Search
CPC . G02C 7/104; G02C 5/20; G02C 5/22; G02C 9/00
USPC .............................................. 351/59, 47, 57
See application file for complete search history.

(56) References Cited

U.S. PATENT DOCUMENTS

| 3,238,005 A * | 3/1966 | Petitto | G02C 9/00 2/13 |
| 3,252,747 A * | 5/1966 | Robins | G02C 7/06 351/57 |
| 6,767,095 B1 * | 7/2004 | Altelaar | G02C 7/16 351/44 |

* cited by examiner

*Primary Examiner* — Hung Dang
(74) *Attorney, Agent, or Firm* — Bardmesser Law Group

(57) ABSTRACT

Rotary eyeglasses comprise a fixed frame bearing a nose abutment and means for holding the eyeglasses on the head, and a movable frame comprising optical members in front of the eyes, when the eyeglasses are in an operational position, wherein the movable frame is secured to the fixed frame by a multi-lever mechanism and is configured to be lifted up relative to the fixed frame and simultaneously to be rotated about its longitudinal axis owing to hinges located in points of securing the levers to the frames. The invention may be used in eyeglasses having positive lenses including reading eyeglasses, and also in protective eyeglasses of different types including sunglasses. The invention allows lifting lenses over the user's forehead, and thus facilitates looking either through lenses or beside lenses, and allows preventing contact between the inner surface of the lenses and the forehead, and thus avoiding contamination of the lenses.

21 Claims, 34 Drawing Sheets

EYEGLASSES WITH A FIXED FRAME AND A ROTATABLE FRAME

CROSS-REFERENCE TO RELATED APPLICATIONS

This application claims priority to RU 2017123756, filed on Jul. 5, 2017, which is incorporated by reference herein in its entirety.

BACKGROUND OF THE INVENTION

Field of the Invention

The invention relates to the field of wearable optics, and, in particular, to eyeglasses.

Background of the Related Art

People suffering from presbyopia and using positive eyeglasses lens to allow focusing eyes on a nearby object do not need to use corrective lens all time, if they have no other eyesight disorders. Therefore, they have to put their eyeglasses on and take them off very often, which is quite inconvenient. When these people want to put on any protective eyeglasses like sunglasses, they also have to take their corrective eyeglasses off.

Using bifocal or progressive lens partially solves this problem for farsighted people, but it decreases a field of view for both near and long distance vision. Using a chameleon lens causes a time lag (1 to 15 minutes) for changing their light transmission degree from transparent to darkened and vice versa. Moreover, even when such photochromic lenses are in a transparent mode, they pass substantially less visible light (about 80%) in comparison to an achromic optical lens of the same thickness (95% to 99%).

US Published Patent Application No. 2012069292 describes a second flat spectacle rim in a form of a hinged visor that is secured to a first flat spectacle rim by means of a sleeve and a shaft. Two spring-loaded cams attached to the sleeve or to the shaft are configured to retain the second rim in an upper position or in a lower position relative to the first rim. These eyeglasses do not allow adjusting angle between the optical axis of an eyeglasses lens and the eyesight axis of an eye. Eyeglasses with a lens in a form of a hinged visor in their upper position deteriorate the user's image, as the hinged-up lenses visibly protrude from the user's forehead line. In such eyeglasses, only one position (the lower position) is provided, in which the eyesight axis of an eye coincide with the optical axis of an eyeglasses lens, so the user may see through the lenses with no eyestrain. This means that the inner surface of the rotatable lens is disposed at a correct angle relative to the eyesight axis of an eye only when the lenses are in their lower position. Even if the hinged lenses are rotated at a tiny angle, the angle between the inner surface and the eyesight axis changes so that intended use of the lenses is difficult or impossible.

Russian patent No. 2146062 describes an embodiment of an eyeglass frame with movable lenses, which is identical to the eyeglasses of US Published Patent Application No. 2012069292; in another embodiment a vertically movable frame with lenses slides up and down along vertical guides mounted on a motionless eyeglass frame, which configuration may cause skewing and jamming the movable frame upon use. Rotation of the frame with lenses relative to its longitudinal axis is not provided.

U.S. Pat. No. 6,767,095 describes eyeglasses with an additional liftable frame which is used as a sun visor, wherein the frame is configured to go up and down owing to presence of articulate joints between ends of the liftable frame and a supporting frame of the eyeglasses. Rotation of the liftable frame relative to its longitudinal axis is not provided, so the upper edge of the liftable frame touches the user's forehead upon lifting the frame. Therefore, the liftable frame may serve as a sun visor only and does not comprise any lenses; otherwise the lenses would be contaminated due to contact with the skin of the user's head upon lifting the frame.

Thus, no eyeglasses suitable for continuous wearing are available, where the eyeglasses would be comfortably used in several positions, when lenses or other optical members are disposed in front of the user's eyes (in a first operational position), or somewhat below the user's eyes (in a second operational position), or removed from the user's eyes (in a non-operational position), while the lenses or other optical members do not touch the skin or hair of the user's head and maintain a usual appearance of the user, as the eyeglasses both in operational and non-operational positions would only slightly visually differ from any ordinary eyeglasses.

SUMMARY OF THE INVENTION

An object of this invention is providing multifunctional eyeglasses ensuring comfortable continuous wearing thereof. This object is achieved by rotary eyeglasses including two frames, one movable and another one fixed, where the movable frame includes optical members and may be lifted up and simultaneously rotated relative to its longitudinal axis so as to adjust an angle between the lens inner surface and an eyesight axis of an eye. It allows providing several positions of the optical members relative to an eye (e.g., a middle position and a lower position) by lifting the movable frame, where the lenses may be used in these positions upon moving eyes upward or downward. If both movable and fixed frames comprise optical members, additional optical effects owing to lens combination may be achieved by lowering the movable frame. For example, for presbyopia, a short-distance eyesight correction may be provided by lowering the movable frame, so two positive lenses are located in front of the user's eye and the optical effect is increased. A mid-distance eyesight correction may be provided by lifting the movable frame, when the eyesight axis of the user's eye passes through only one lens mounted on the fixed frame. For long-distance vision, the movable frame may also be lifted and the user may look above the lens mounted on the fixed frame.

If the optical members of the movable frame are displays and the fixed frame has lenses for additional accommodation for the displays, the user may read some information from the displays that does not require high definition (like arrows denoting direction of movement, speed indication numbers, etc.) by moving his eyes up, when the movable frame is lifted up. When the movable frame is lowered so that a positive lens mounted on the fixed frame is disposed between the display and the user's eye, an image requiring high definition may be outputted to the display. If the displays are transparent or semi-transparent, it may be expedient to equip them with photochromic elements.

When the movable frame is in an upper position, the optical members should be disposed in parallel with the user's forehead, and never protrude far from the head surface. At the same time, the optical members should not touch the forehead skin so as to avoid contamination of the optical members.

One of the objects of the invention is achieved by providing rotary eyeglasses including a fixed frame having left and right lateral ends; a nose abutment connected to the fixed frame at substantially equal distance from the lateral ends; right and left bows connected to the left and right lateral ends of the fixed frame, respectively; a movable frame having left and right lateral ends and comprising at least two optical members; left and right arms each having a distal end and a proximal end. The proximal ends of the left and right arms are articulated to the left and right lateral ends of the fixed frame, respectively, and the distal ends of the left and right arms are articulated to the left and right lateral ends of the movable frame, respectively, so the articulated joints provide rotation of the left and right arms substantially in parasagittal planes.

It is recommended to locate the points of the articulated joints between the arms and the lateral ends of the fixed frame at a vertical distance not greater than 20 mm from the horizontal eye axis. It is preferable to locate the points of the articulated joints between the arms and the lateral ends of the fixed frame above the horizontal eye axis. It is advantageous that the eyeglasses further comprise at least one means for locking the movable frame in any position among available positions.

It is recommended to provide the optical members in a form of optical lenses, protective glass elements or displays for displaying visual information to the user. It is also recommended to provide the movable frame being adjustable according to a distance between the pupils. It is also advantageous that the fixed frame further comprises optical members disposed in front of the user's eyes.

In one preferred embodiment, the eyeglasses may further comprise at least two tubular sheaths (left and right), configured so that the left and right sheaths encompass the left and right arms, respectively, when the eyeglasses are in an operational position; the left and right sheaths encompass the optical members, when the eyeglasses are in a non-operational position in order to protect the optical members against damage and contamination.

The object is also achieved by providing rotary eyeglasses including a fixed frame having left and right lateral ends; a nose abutment connected to the fixed frame at substantially equal distance from the lateral ends; a movable frame having left and right lateral ends and comprising at least two optical members; upper left arm, lower left arm, upper right arm, and lower right arm, each having a distal end and a proximal end. The proximal ends of the upper and lower left arms and the upper and lower right arms are vertically spaced from each other and are articulated to the left and right lateral ends of the fixed frame, respectively, and the distal ends of the upper and lower left arms and the upper and lower right arms are vertically spaced from each other and are articulated to the left and right lateral ends of the movable frame, respectively, so the upper and lower left arms and the upper and lower right arms and corresponding portions of the right and left lateral ends of the movable frame between the articulated joints, and corresponding portions of the right and left lateral ends of the fixed frame between the articulated joints form four-link lever mechanisms substantially disposed in parasagittal planes.

It is advantageous that the points of the articulated joints between the arms and the lateral ends of the movable frame at the left and right sides are located at a distance not greater than 20 mm from each other. It is also advantageous that an angle of rotation of the arms relative to the fixed frame is in a range of 10 to 25 degrees. It is recommended to provide the optical members in a form of optical lenses, protective glass elements or displays for displaying visual information to the user. It is also recommended to provide the movable frame being adjustable according to a distance between the pupils.

It is advantageous that the fixed frame further includes optical members disposed in front of the user's eyes. It is advantageous that the rotary eyeglasses further include a cord, which ends are connected to the proximal ends of the bows.

In one preferable embodiment, the eyeglasses may further include at least two tubular sheath, left and right, configured so as the left and right sheaths encompass the upper and lower left arms and the upper and lower right arms, respectively, when the eyeglasses are in an operational position; the left and right sheaths encompass the optical members, when the eyeglasses are in a non-operational position in order to protect the optical members against damage and contamination.

In another preferable embodiment, the eyeglasses may further include at least two tubular sheath, left and right, configured so as the left and right sheaths encompass the left and right bows, respectively, when the eyeglasses are in an operational position; the left and right sheaths encompass the optical members, when the eyeglasses are in a non-operational position in order to protect the optical members against damage and contamination.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification and together with the description serve to explain the principles of the invention.

DETAILED DESCRIPTION OF THE PREFERRED EMBODIMENTS

Figure 1:
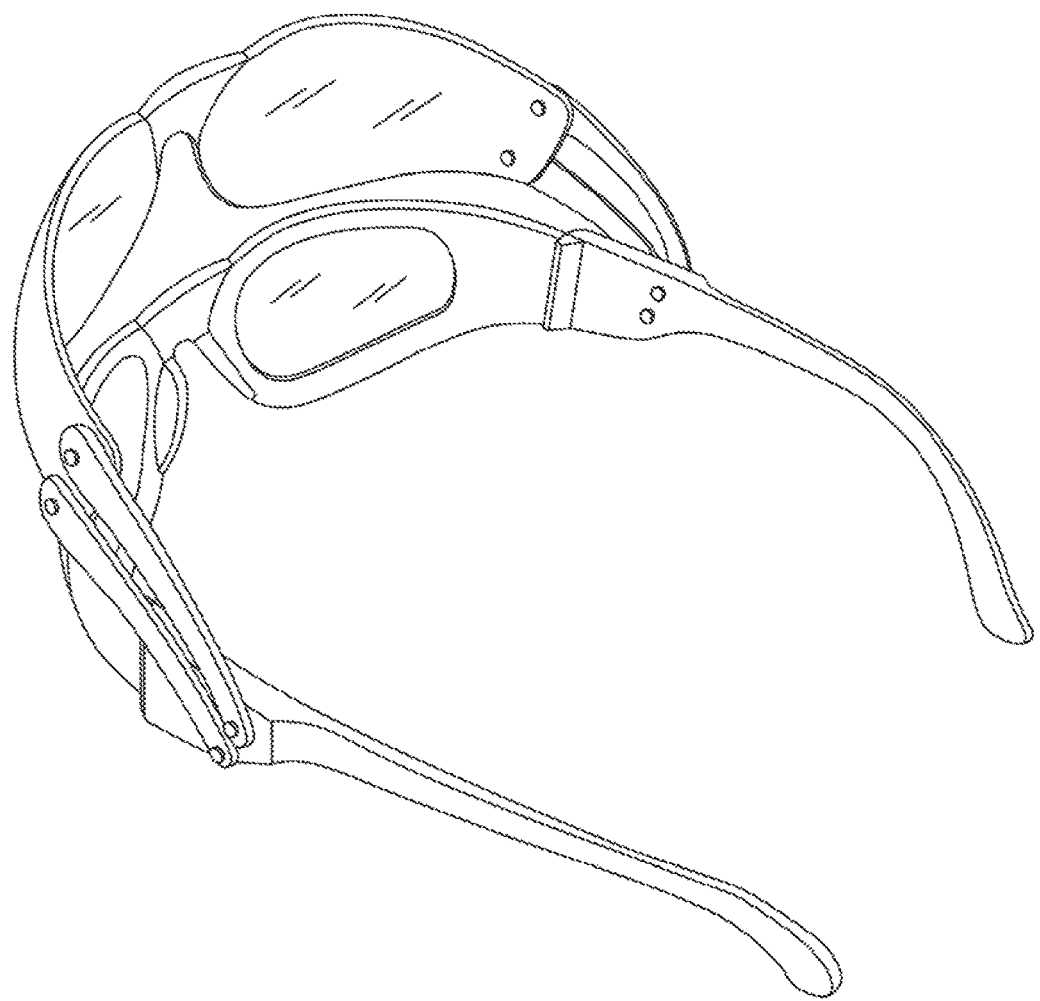
FIG. 1 shows a general view of rotary eyeglasses having four arms, according to the invention.

Reference will now be made in detail to the preferred embodiments of the present invention, examples of which are illustrated in the accompanying drawings.

The images in the drawings are in schematic form, therefore they show only those parts of the invention, which are important for implementation of the invention by a person of ordinary skill in the art, and the less important parts or components are not shown in the drawings.

Expressions denoting orientation or direction like upward, downward, forward, backward, left, right shall be understood relative to head of a human in a vertical position, when eyes are in their natural position, eyesight is directed straight to an object located at eye level, the head is oriented straight forward with no any tilt or rotation, unless the context explicitly indicates otherwise.

The following ophthalmology expressions are used for denoting position of the eyes, which may be different from commonly used terminology:
- an anatomic (sagittal) eye axis is a line connecting its poles;
- an eye rotation center is a point located in immediate vicinity of the middle of a sagittal axis segment located between the eye poles;
- a vertical axis is a line passing through the eye rotation center in perpendicular to the sagittal axis;
- a horizontal transversal axis is a line perpendicular to the vertical axis and the sagittal axis.

Rotary eyeglasses of one embodiment of the invention (see FIGS. 1, 2, 3) comprise a fixed frame 1 with a nose abutment (nose pads) 2 in the middle and bows 3A, 3B connected to lateral ends of the fixed frame. The rotary eyeglasses also comprise a movable frame 4 with optical members 5A, 5B, right arm 6A and left arm 6B, where each arm has a distal end and a proximal end. The proximal end of the right arm 6A is connected to the right lateral side of the fixed frame 1 by a hinge 7A, and the proximal end of the left arm 6B is connected to the left lateral side of the fixed frame 1 by a hinge 7B so as to ensure transversal rotation of the arms about a longitudinal axis of the fixed frame passing through the hinge centers. The distal end of the right arm 6A is connected to the right lateral side of the movable frame 4 by a hinge 8A, and the distal end of the left arm 6B is connected to the left lateral side of the movable frame 4 by a hinge 8B so as to ensure rotation of the movable frame 4 about a longitudinal axis of the movable frame.

Figure 3:
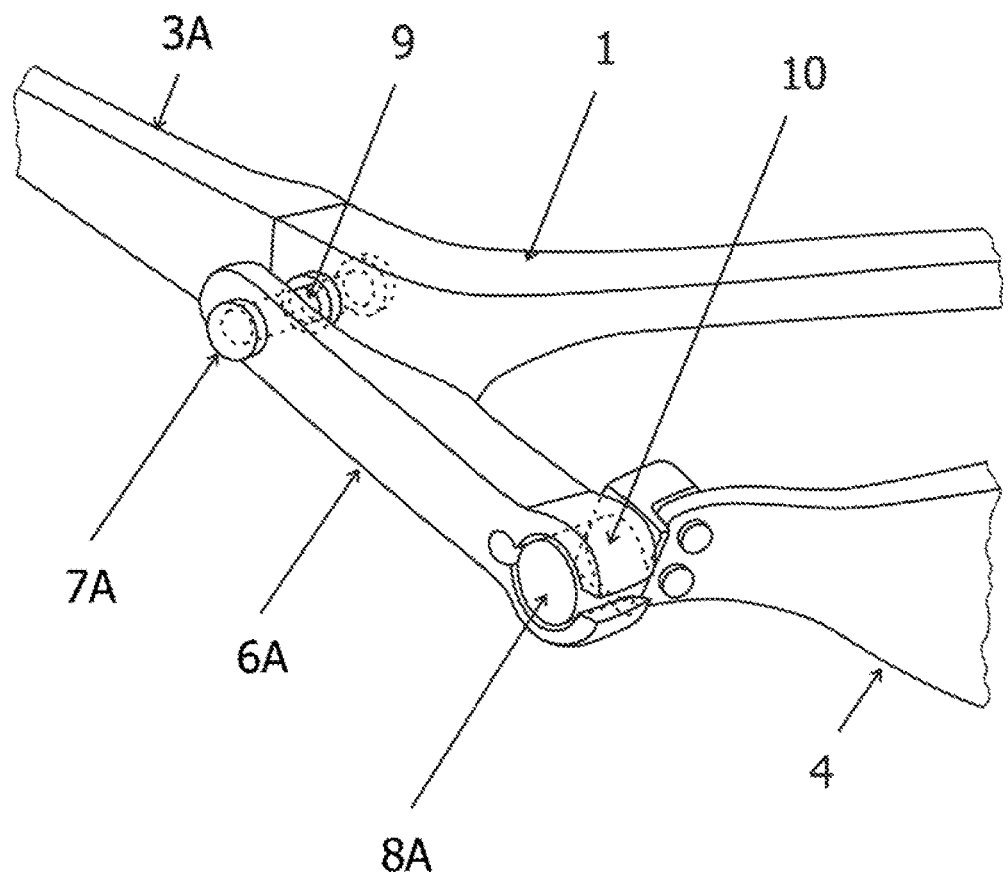
FIG. 3 shows an embodiment of a lever mechanism, according to the invention.

FIG. 3 shows detailed configuration of a joint of the movable frame 4 and the fixed frame 1 provided by the arm 6A in an embodiment, where the hinge 7A provides movement of the movable frame 4 relative to the fixed frame 1 via pins 9 and 10.

Figure 4:
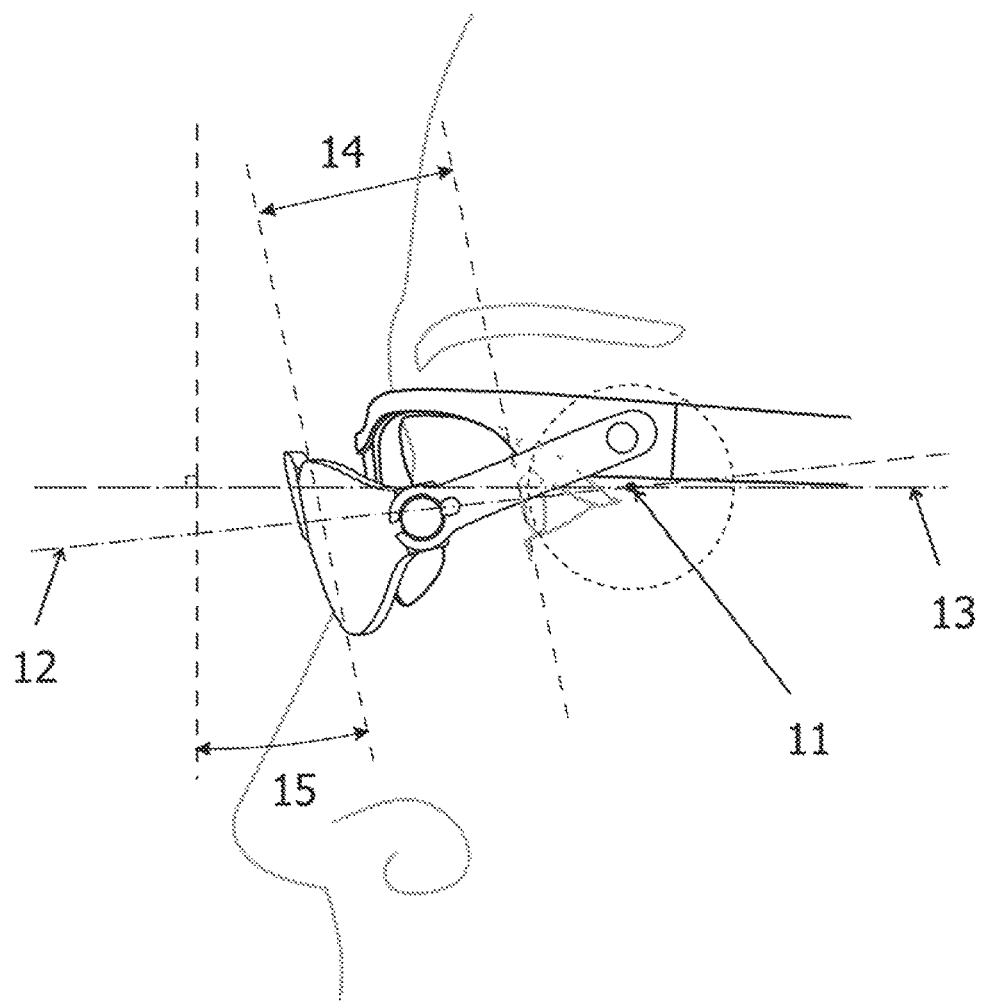
FIG. 4 shows rotary eyeglasses according to the invention in an operational position on a user and main parameters used for designing the eyeglasses.

The proposed eyeglasses allow people suffering from presbyopia to have a wide field of short-distance vision at a middle or lower position of the movable frame, when the lenses are positioned in front of eyes or somewhat lower. This configuration allows maintaining a required vertex distance and an appropriate pantoscopic angle. FIG. 4 shows rotary eyeglasses according to the invention in a lower operational position on a user and the following main details used for designing the eyeglasses: an eye rotation center 11, an eyesight axis 12, a sagittal axis 13, a vertex distance 14 (i.e., a distance between the eyeball vertex and the inner (i.e., facing the eye) surface of a lens), and a pantoscopic angle 15.

If a two-arm rotation mechanism is used for rotating the movable frame, where each arm is connected to each frame by a hinge and the hinges connect distal ends of the right and left arms to the lateral left and right sides of the movable frame, respectively, the pantoscopic angle may be adjusted according to anatomic features and preferences of a user. When the movable frame is lifted up, the hinge allows placing the eyeglasses' lenses in parallel to the forehead surface at a sufficient distance from the forehead, so that the inner surfaces of the lenses do not contact the skin and contamination of the lenses may be avoided. It is ensured by a configuration, in which the movable frame is able to go up and down in a vertical plane and additionally is able to rotate about its longitudinal axis due to an articulated link connecting the movable frame to the fixed frame of the eyeglasses.

It is known that certain conditions should be applied while selecting a spectacle frame and determining if it fits the user's face, taking into account mutual position of lenses and eyes. Standard conditions are as follows: a vertex distance should be in a range of 12 to 15 mm; a pantoscopic angle should be in a range of 8 to 12 degrees; a bend angle of the frame should be in a range of 4 to 5 degrees. These conditions are treated as universal and often applied for eyeglasses having either positive or negative lenses. However, people suffering from presbyopia and people suffering from myopia use their eyeglasses in different ways. When using positive lenses, a user looks mostly downward, e.g., when the user sits at a table. Meanwhile, the user simultaneously tilts the head approximately by 15 degrees relative to a horizontal line and casts eyes down approximately by 15 degrees in a vertical plane. The head tilt may be neglected during designing eyeglasses, but the downcast eye pitch angle increases an angle between the optical axis of a lens and the eyesight axis of an eye.

In practice, when a spectacle frame is selected, the pantoscopic angle is mostly assumed to be an angle between the optical axis of a lens and the eyesight axis in a neutral position of an eye (i.e., when eyesight is directed horizontally forward). If an eye is downcast as described in the above, the angle between the optical axis of a lens and a horizontal line, when the eye is in a neutral position (i.e., when eyesight is directed horizontally forward), should be increased in order to maintain the angle between the optical axis of the lens and the eyesight axis of the eye unchanged. The Applicant's calculations show that this angle should be in a range of 15 to 25 degrees for positive lenses, i.e., somewhat greater than the standard value of 8 to 12 degrees used for any types of eyeglasses, in which the eyesight axis of an eye is supposed to be near horizontal.

Figure 8:
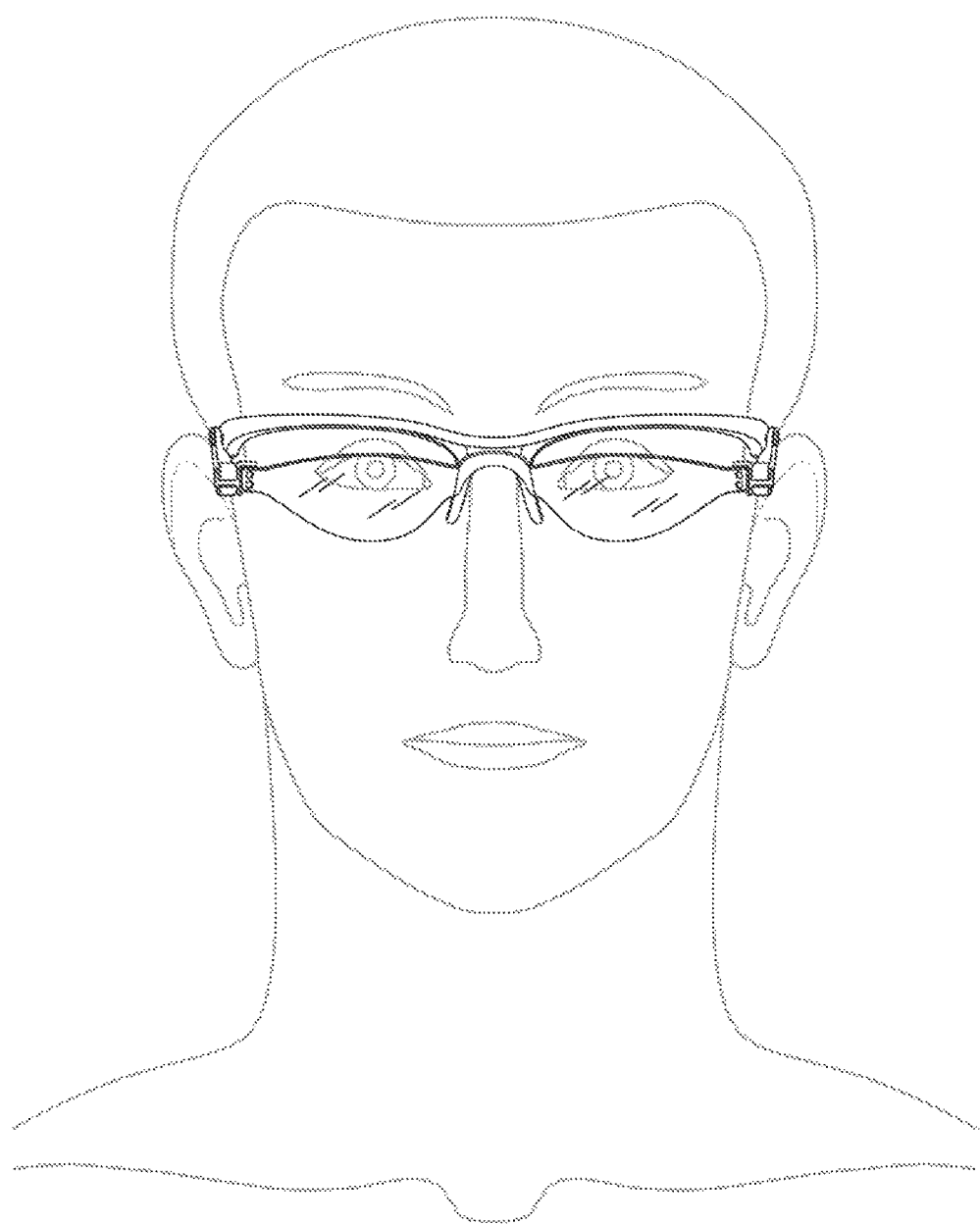
Figure 9:
FIG. 9 shows rotary eyeglasses according to the invention in a lowermost position on a user.

Additionally, an interpupillary distance is less in case of eyeglasses for presbyopia, than in case of eyeglasses for myopia. Moreover, for presbyopia correction, there is no need to use lenses providing wide field of vision, so eyeglasses may be made with lenses of less dimensions. It is may be quite enough to use lenses having 3 to 4 cm of horizontal dimension and about 2 cm of vertical dimension. According to these circumstances, rotary eyeglasses having a movable frame are provided, which eyeglasses allow changing position of the movable frame and do not deteriorate the user's appearance much. If lenses having small vertical dimension are used, the lowest position of the movable frame provides so-called "lecturer" mode of the eyeglasses, when the user may cast eyes down to read at a short distance, and may look at a long-distance object above the lenses. In other words, three positions of the movable frame are available:

- an uppermost position (FIGS. 5, 6), when the lenses are out of sight of the user;
- a middle position (FIGS. 7, 8), when the lenses are disposed in front of eyes of the user and the eyesight axis of the eye is near horizontal;
- a lowermost position (FIG. 9), which may be called a "lecturer" position.

The following initial data were used for modelling the lifting mechanism of the eyeglasses. It is necessary to maintain the vertex distance in an operation position of a lens; the pantoscopic angle and anatomic features of the user's head also have to be taken into account. When eyeglasses are worn with the movable frame in its lowest position (when the movable frame is positioned lower the fixed frame), the pantoscopic angle should not exceed 27 degrees relative to the sagittal eye axis in the natural position of the eye, and 12 degrees relative to the sagittal eye axis, when the eye is downcast for about 15 degrees, in comparison to the natural position.

If age-related presbyopia is not accompanied with other vision disorders like astigmatism or myopia, it is recommended to limit maximum height of the lenses to 20 mm.

Figure 10:
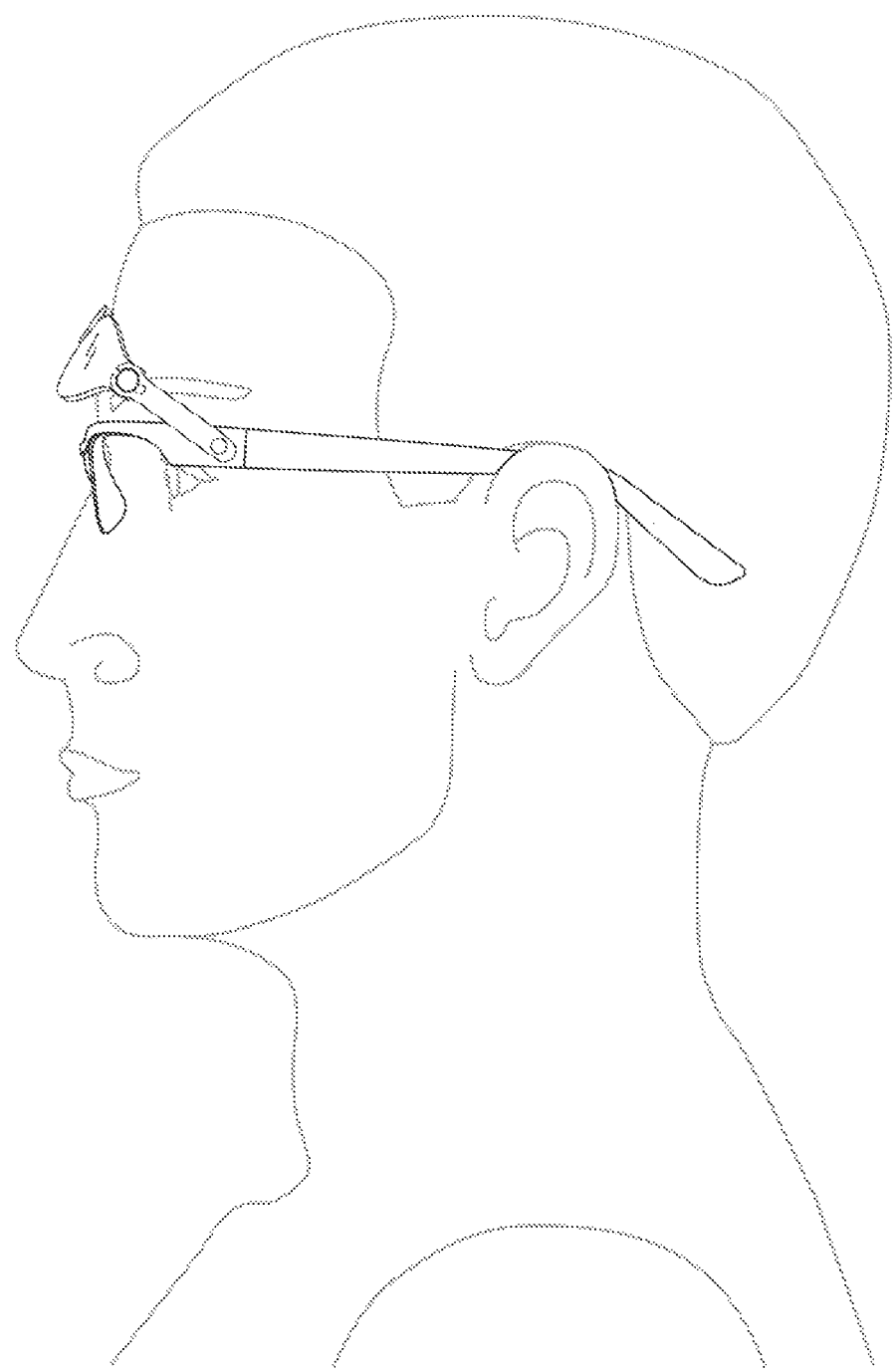
FIG. 10 shows rotary eyeglasses according to the invention in a non-adjusted upper position on a user.

When in a non-operational position, the lenses should be located out of the user's field of vision and positioned in parallel to the user's forehead surface at a certain distance from the forehead skin so as to avoid contamination of the lenses. This contamination is possible when the lenses are located as shown in FIG. 10. When in the uppermost position, the optical members (e.g., lenses) shall be positioned at a sufficient distance from the forehead so as to avoid contamination of the optical members due to the user's mimic/muscular movement of expression.

Figure 11:
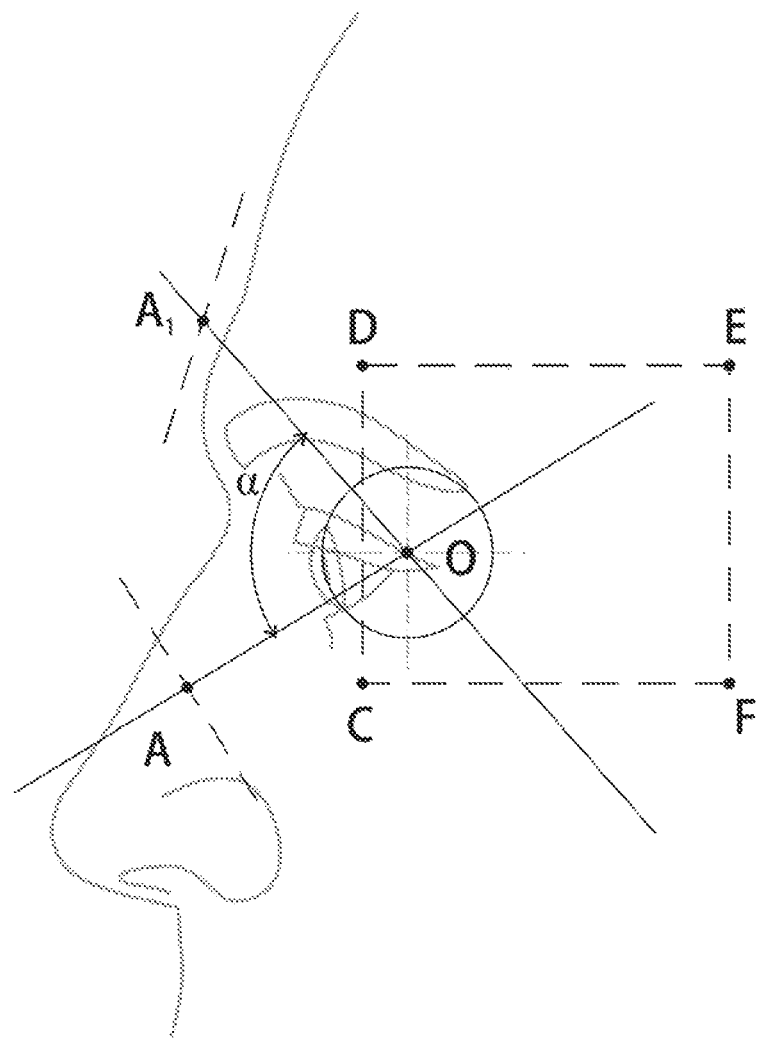
FIG. 11 shows a profile view of a model of the user's head with the sagittal cross-section of the eye.

FIG. 11 shows a profile view of a model of the user's head with the sagittal cross-section of the eye.

A two-dimensional solution needs to be found, where all elements of the eyeglasses mechanism are projected to a plane corresponding to the sagittal cross-section passing through the rotation center of the eye. A cross point of the eyesight axis and the inner surface of the lens moves in this plane, when the eye moves up and down. The rotation center of the eye is defined as the reference point of design. Suppose axis X is directed along the anatomic (sagittal) axis of the eye, and axis Y is directed along the vertical axis of the eye. Dashed lines passing through points A and $A_1$ denote the inner surface of the lens in its sagittal cross-section passing through the rotation center.

When designing eyeglasses having foldable bows, it is expedient to avoid placing points of connection of proximal hinges of the arms on the foldable bows. Upon analyzing a sample set of anatomical dimensions of user heads and traditional design of eyeglasses, the Applicant found that possible connection points of the proximal hinges of the arms are located in area CDEF shown in FIG. 11. If certain conditions are met (conditions regarding the vertex distance, the pantoscopic angle and the lens height), axes of the proximal hinges shall be placed in an area having coordinate X in a range of −6 mm to +45 mm, and coordinate Y in a range of −20 mm to +26 mm.

Suppose uplifting the lens in vertical plane according a horizontal axis may be considered as rotation of the lens about point O, with distance OA being less than distance $OA_1$. Coordinates of a point where the point O shall move so as to satisfy the condition of $|OA|=|OA_1|$ have to be calculated, where the new coordinates of the point O are located in area CDEF.

First, a one-arm lifting mechanism shall be modelled, wherein one hinge is fastened to the movable frame edge, and another hinge is fastened to the fixed frame, taking into account the above-stated design conditions. It is tentatively assumed that the lens and the movable frame are flat in the frontal plane.

A condition of maintaining the arm length while moving from point A to point $A_1$ (i.e., rotation about point O, see FIG. 12) is applied:

$$\sqrt{(x_O-x_{A1})^2-(y_O-x_A)^2}=\sqrt{(x_O-x_A)^2-(y_O-y_A)^2} \quad (1)$$

where $x_O$, $y_O$ are coordinates of point O $x_A$, $y_A$ are coordinates of initial point A $x_{A1}$, $y_{A1}$ are coordinates of final point A (i.e., $A_1$); therefore $$(x_O - x_{A1})^2 - (y_O - y_{A1})^2 = (x_O - x_A)^2 - (y_O - y_A)^2 \quad (2)$$

$$x_O^2 - 2x_O x_{A1} + x_{A1}^2 + y_O^2 - 2y_O y_{A1} + y_{A1}^2 = \quad (3)$$
$$x_O^2 - 2x_O x_A + x_A^2 + y_O^2 - 2y_O y_A + y_A^2$$

$$-2x_O x_{A1} + x_{A1}^2 + y_{A1}^2 + 2x_O x_A - x_A^2 - y_A^2 = 2y_O(y_{A1} - y_A) \quad (4)$$

$$y_O = \frac{x_O(x_A - x_{A1}) + (x_{A1}^2 - x_A^2)}{y_{A1} - y_A} + \frac{y_{A1} + y_A}{2} \quad (5)$$

Thus, equation (5) of a line is found, wherein the first term is tangent of an inclination angle, and the second term is responsible for shift relative to the reference point. Placing the connection point of the arm on a segment of the line within area CDEF resolves the above conditions. More precise selection of the connection point may be done based on exact configuration of the eyeglasses, depending on the lens height and the place of securing the lifting arms to the movable frame.

Figure 12:
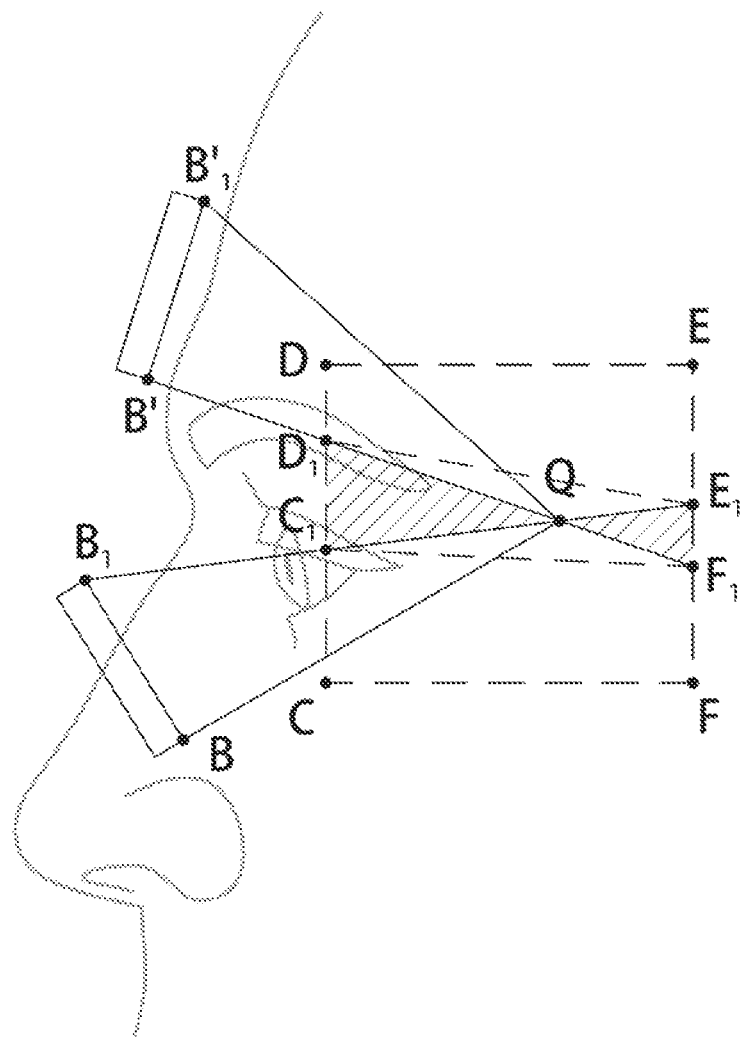
FIGS. 12 and 13 show two utmost positions of a lens on a model of the user's head.

In this case suppose that the optimal height of the lens $BB_1$ is not greater than 25 mm, and the lifting angle of the lens is not greater than 85 degrees (FIG. 12). All possible places of points of securing the arms to the movable frame (points A) are located on segment $BB_1$.

By using the defined substitutional values and solving equation (5), area CDEF (projection of securing the arm pin to the fixed frame) may be reduced to area $C_1D_1QE_1F_1$, which further may be optimized to area $C_1D_1Q$, wherein point Q is a projection of the fixed frame hinge on the sagittal plane opposite to a temporal region near the frontal bone zygomatic process.

Further, optimization of calculation of the one-arm lifting mechanism model will be considered.

Figure 13:
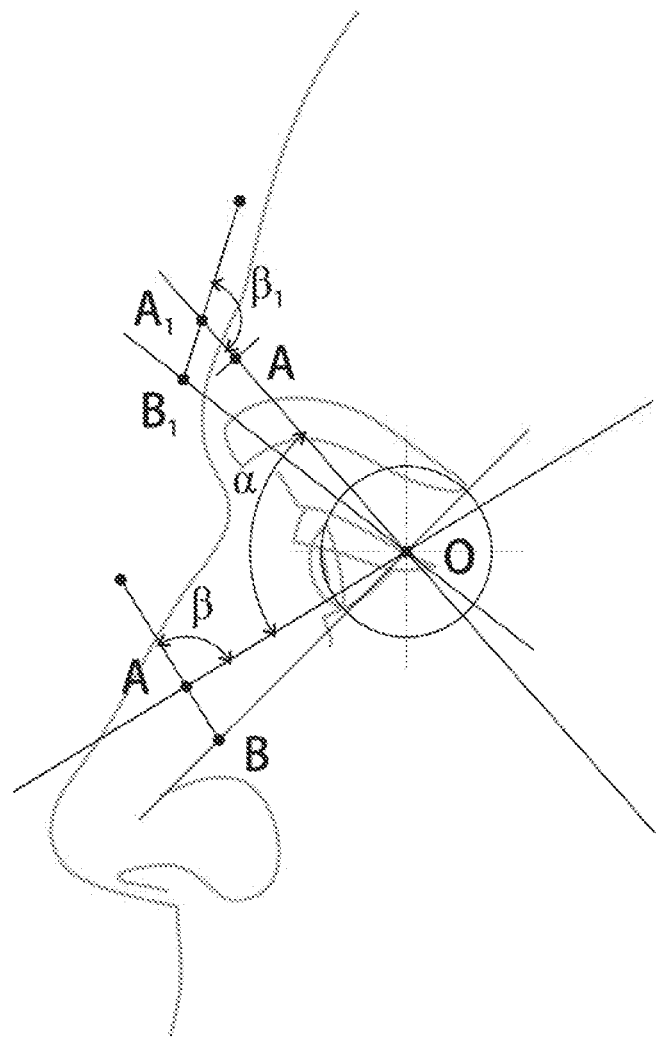

Two ultimate positions of the lens are already defined (see FIGS. 12, 13). Transition of the lens from its initial position to its final position may be considered as a superposition of the following movements:

first, rotation of point A around point O; but in this case point A would penetrate into the forehead, so in order to avoid this, it is necessary to increase the length of OA to the length of $OA_1$ or change the position of point O; therefore second, the length of OA has to be changed, i.e., point A should be shifted to $A_1$.

Optimal lens height is 25 mm, and this means that the movable frame has to be rotated about its longitudinal axis passing through the hinge securing the arm to the movable frame, which corresponds to change angle $\beta$ to angle $\beta_1$ in the model; and third, the lens thus rotates about the new position of point A (i.e., about point $A_1$).

The simplest way of representing these operations is defining coordinates of a point in a form of a two-dimensional vector and multiplying this vector by a corresponding matrix for each operation (e.g., rotation or shift), thus obtaining a new vector (i.e., new coordinates of the point) (see FIG. 13).

A matrix corresponding to clockwise rotation by angle $\alpha$ is as follows:

$$M(\alpha) = \begin{matrix} \cos\alpha & \sin\alpha \\ -\sin\alpha & \cos\alpha \end{matrix} \qquad (6)$$

Coordinates of point $A_1$ may be found:

$$\begin{pmatrix} x_{A1} \\ y_{A1} \end{pmatrix} = \begin{pmatrix} \cos\alpha & \sin\alpha \\ -\sin\alpha & \cos\alpha \end{pmatrix} \cdot \begin{pmatrix} x_A \\ y_A \end{pmatrix} \qquad (7)$$

The following equations may be obtained by multiplying the matrix:

$$x_{A1} = x_A \cos \alpha + y_A \sin \alpha \qquad (8)$$

$$y_{A1} = -x_A \sin \alpha + y_A \cos \alpha \qquad (9)$$

Figure 14:
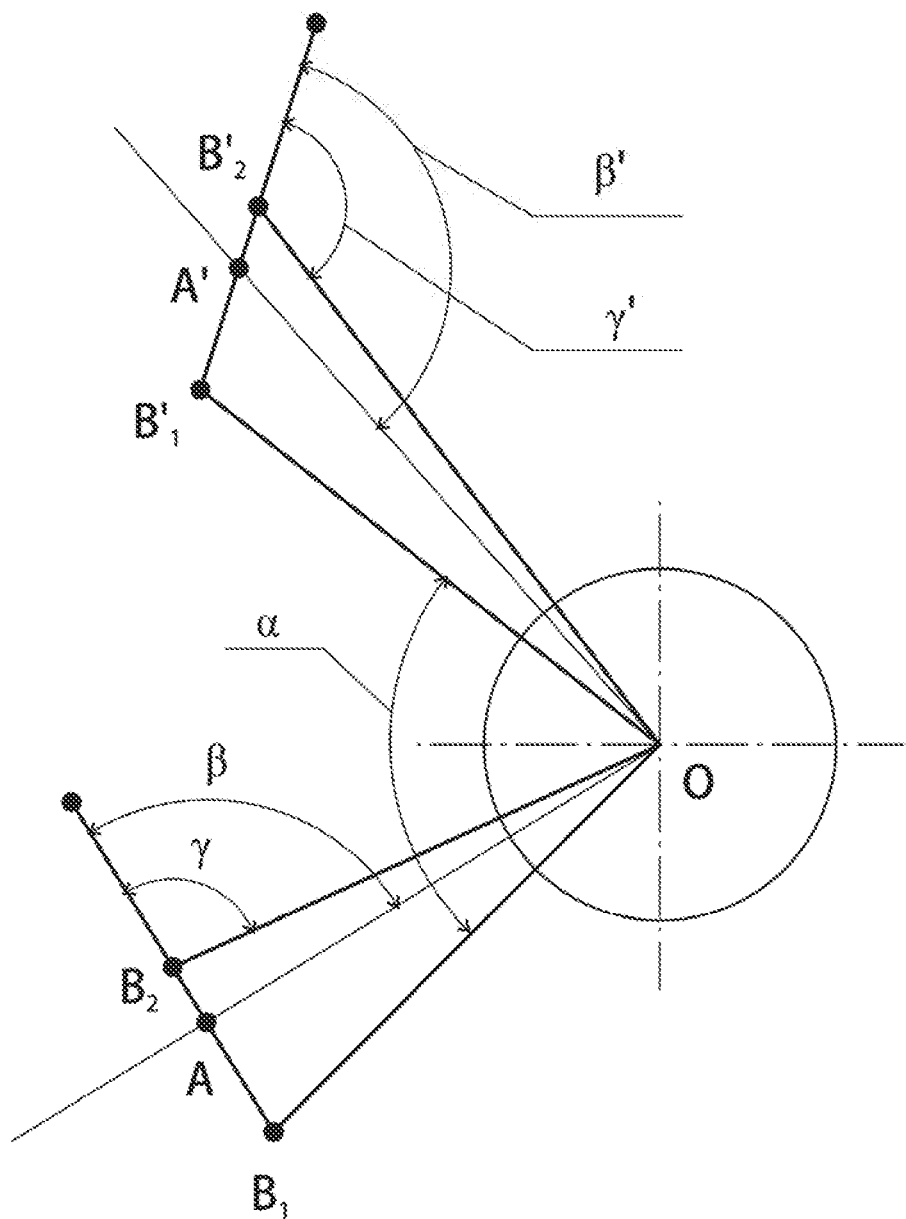
FIG. 14 illustrates a mathematical model for calculating a lens rotation angle, according to the invention.

Rotation around an arbitrary point corresponds to rotation around the reference point as shown in expressions (6) to (9), but with coordinates of the rotation center point observed. For example, for rotation of point $A_1$ about point $B_1$ by an angle $\beta$ (see FIG. 14) the following results:

$$x_{A3} = x_{B2} + (x_{A2} - x_{B2}) \cdot \cos \beta + (y_{A2} - y_{B2}) \cdot \sin \beta \qquad (10)$$

$$y_{A3} = y_{B2} - (x_{A2} - x_{B2}) \cdot \sin \beta \alpha (y_{A2} - y_{B2}) \cdot \cos \beta \qquad (11)$$

where $x_A$, $y_A$ are coordinates of an initial point (point A), $x_{A1}$, $y_{A1}$ are coordinates of a new position of point A after the first movement (i.e., point $A_1$), $x_{A2}$, $y_{A2}$ are coordinates of a new position of point A after the second movement (i.e., point $A_2$), $x_{A3}$, $y_{A3}$ are coordinates of a new position of point A after the third movement (i.e., point $A_3$).

According to the law of sines, the following expression may be found from triangle $OB_2'A'$:

$$\frac{OB_2'}{\sin\beta'} = \frac{OA'}{\sin(180° - \gamma')} \qquad (12)$$

Given that sin $(180-\gamma')=-\sin (\gamma')$, sin $(-\gamma')=-\sin (\gamma')$, expression (12) produces the following result:

$$OA' = \frac{-OB_2' \cdot \sin\gamma'}{\sin\beta'} \qquad (13)$$

If angle $\gamma$ itself has to be determined, then:

$$\gamma' = -\sin^{-1}\left(\frac{-OA' \cdot \sin\beta'}{OB_2'}\right) \qquad (14)$$

Two different solutions may be used for providing rotation of the lens by angles $\beta$ and $\beta'$ relative to the arm. In a simpler embodiment, changing angle $\beta$ to angle $\beta'$ is provided by an additional hinge located in the point of connection between the arm and the movable frame, the hinge ensuring rotation of the movable frame around its longitudinal axis passing through the hinge center. However, with this solution, a user has to perform an additional movement for rotating the lenses; moreover, some skew between the movable frame and the arms may occur.

These disadvantages may be avoided in a more complex embodiment, wherein rotation of the movable frame is provided not about its longitudinal axis passing through the hinge center, but via a path defined by hinges in the rotational mechanism based on two-beam articulated four-link lever mechanism (which sometimes may be a pantograph) ensuring required movement manner of the movable frame in two planes.

Analysis performed for a one-arm mechanism allows determining dimensions and coordinates of the ends of one beam.

Therefore, in order to design the four-link lever mechanism, a length of the other beam and location of its hinges have to be determined, taking into account constraints of the lens height (i.e., maximal coupler length) and the bar length (distance between the points of connection of the lever hinges to the fixed frame), which has to be within area CDEF and cannot exceed 20 mm.

Figure 15:
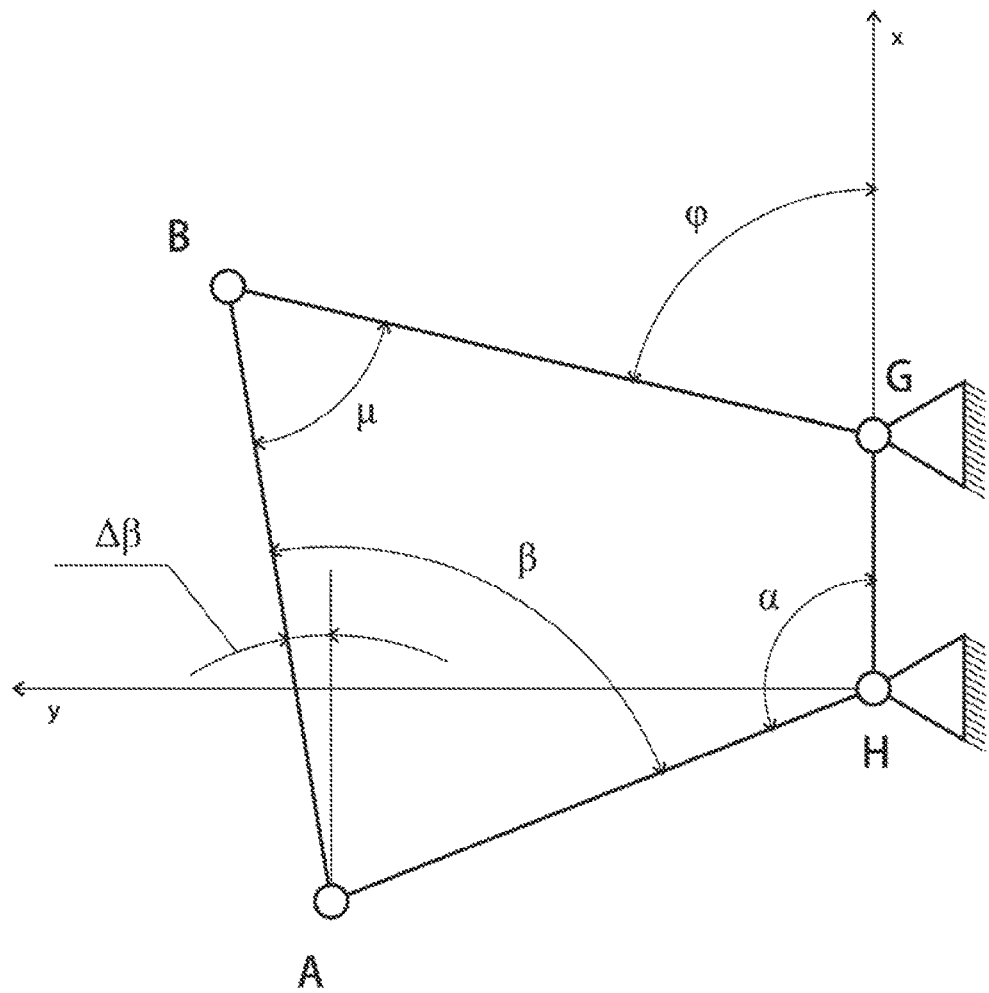
FIG. 15 illustrates a kinematical model for calculating a four-link lever mechanism, according to the invention.

Thus, in order to design the four-link lever mechanism (shown in FIG. 15), the following equations may be defined:

projecting segments of the links onto axis Y:

$$HA \cdot \sin \alpha - AB \cdot \sin \Delta\beta = BG \cdot \sin \varphi \qquad (15)$$

$$AB \cdot \sin \Delta\beta = HA \cdot \sin \alpha - BG \cdot \sin \varphi \qquad (16)$$

$$(AB \cos \Delta\beta)^2 = (HG + BG \cdot \cos \varphi - HA \cdot \cos \alpha)^2 = HG^2 + \\ 2 \cdot HG \cdot BG \cdot \cos \varphi - 2 \cdot HG \cdot HA \cdot \cos \alpha + BG^2 \cdot \cos^2\varphi - \\ 2 \cdot HA \cdot DG \cdot \cos \varphi \cdot \cos \alpha + HA^2 \cdot \cos^2\alpha \qquad (17);$$

projecting segments of the links onto axis X:

$$HA \cdot \sin \alpha - AB \cdot \sin \Delta\beta = BG \cdot \sin \varphi \qquad (18)$$

$$AB \cdot \sin \Delta\beta = HA \cdot \sin \alpha - BG \cdot \sin \varphi \qquad (19)$$

$$(AB \cdot \sin \Delta\beta)^2 = (HA \cdot \sin \alpha - BG \cdot \sin \varphi)^2 = HA^2 \sin^2\alpha + BG^2 \cdot \sin^2\varphi + 2 \cdot HA \cdot BG \cdot \sin \alpha \cdot \sin \varphi \qquad (20);$$

summing equations (17) and (20):

$$AB^2 = AH^2 + BG^2 + HG^2 + 2 \cdot HG \cdot BG \cdot \cos \varphi \cdot 2 \cdot HG \cdot HA \cdot \cos \alpha - 2 \cdot HA \cdot BG \cdot \cos \varphi \cdot \cos \alpha - 2 \cdot HA \cdot BG \cdot \sin \alpha \cdot \sin \varphi \qquad (21)$$

transforming expression (21) into this form:

$$\frac{HA^2 - AB^2 + BG^2 + HG^2}{2 \cdot HA \cdot BG} + \frac{HG}{HA} \cdot \cos\varphi - \frac{HG}{BG} \cdot \cos\alpha - \cos\alpha \cdot \cos\varphi - \sin\alpha \cdot \sin\varphi = 0 \qquad (22)$$

defining terms of expression (22) in this way:

$$k_1 = \frac{HA^2 - AB^2 + BG^2 + HG^2}{2 \cdot HA \cdot BG}; k_2 = \frac{HG}{HA}; \qquad (23)$$

$$k_3 = \frac{HG}{BG}$$

and finally resulting in:

$$k_1 + k_2 \cdot \cos \varphi - k_3 \cdot \cos \alpha = -\cos(\alpha + \varphi). \qquad (24)$$

The resulting equation contains three parameters $k_1$, $k_2$ and $k_3$, which are link lengths; accordingly, it is necessary to define three positions of the mechanism in order to compose and solve a corresponding equation set. Constraints have to be defined in order to avoid an infinite number of solutions. In this case, the constraints comprise an area, in which the hinges are disposed, extreme positions of the mechanism, and possible positions of the hinges relative to each other.

Equation (24) is a Friedenstein equation and $k_1$, $k_2$ and $k_3$ are Friedenstein factors. The equation allows solving the problem of designing a four-link lever mechanism, if some positions of a guide link and a follower link are known. For example, three predetermined positions of the guide link and the follower link allow defining the following angle parameters:

$\alpha_1$, $\alpha_2$, $\alpha_3$ are three positions of the guide link;
$\varphi_1$, $\varphi_2$, $\varphi_3$ are three positions of the follower link.

These initial data produce the following equation set:

$$\begin{cases} k_1 + k_2 \cdot \cos\varphi_1 - k_3 \cdot \cos\alpha_1 = -\cos(\varphi_1 + \alpha_1) \\ k_1 + k_2 \cdot \cos\varphi_2 - k_3 \cdot \cos\alpha_2 = -\cos(\varphi_2 + \alpha_2) \\ k_1 + k_2 \cdot \cos\varphi_3 - k_3 \cdot \cos\alpha_3 = -\cos(\varphi_3 + \alpha_3) \end{cases} \qquad (25)$$

Equation set (25) may be represented in a matrix form like $A \times k = b$, wherein $$A = \begin{bmatrix} 1 & \cos\varphi_1 & -\cos\alpha_1 \\ 1 & \cos\varphi_2 & -\cos\alpha_2 \\ 1 & \cos\varphi_3 & -\cos\alpha_3 \end{bmatrix}; k = \begin{bmatrix} k_1 \\ k_2 \\ k_3 \end{bmatrix}; b = \begin{bmatrix} -\cos(\varphi_1 + \alpha_1) \\ -\cos(\varphi_2 + \alpha_2) \\ -\cos(\varphi_3 + \alpha_3) \end{bmatrix} \qquad (26)$$

Finding solution to the equation set in a general form:

$$k = A^{-1} \cdot b \qquad (27)$$

Further, based on the found Friedenstein factors, dimensions of the links in the four-link lever mechanism may be found:

$$HG = 1; HA = \frac{HG}{k_2}; \qquad (28)$$

$$AB = \frac{\sqrt{k_2^2 + k_3^2 + k_2^2 \cdot k_3^2 - 2 \cdot k_1 \cdot k_2 \cdot k_3}}{k_2 \cdot k_3}; BG = \frac{HG}{k_3}$$

The dimensions are denominated in millimeters, according to the base measurement units selected due the scale and estimate size of the mechanism under design.

Based on the above equations, an optimized lifting mechanism may be designed using an appropriate mathematical software tool like MathCAD or MatLab.

Figure 16:
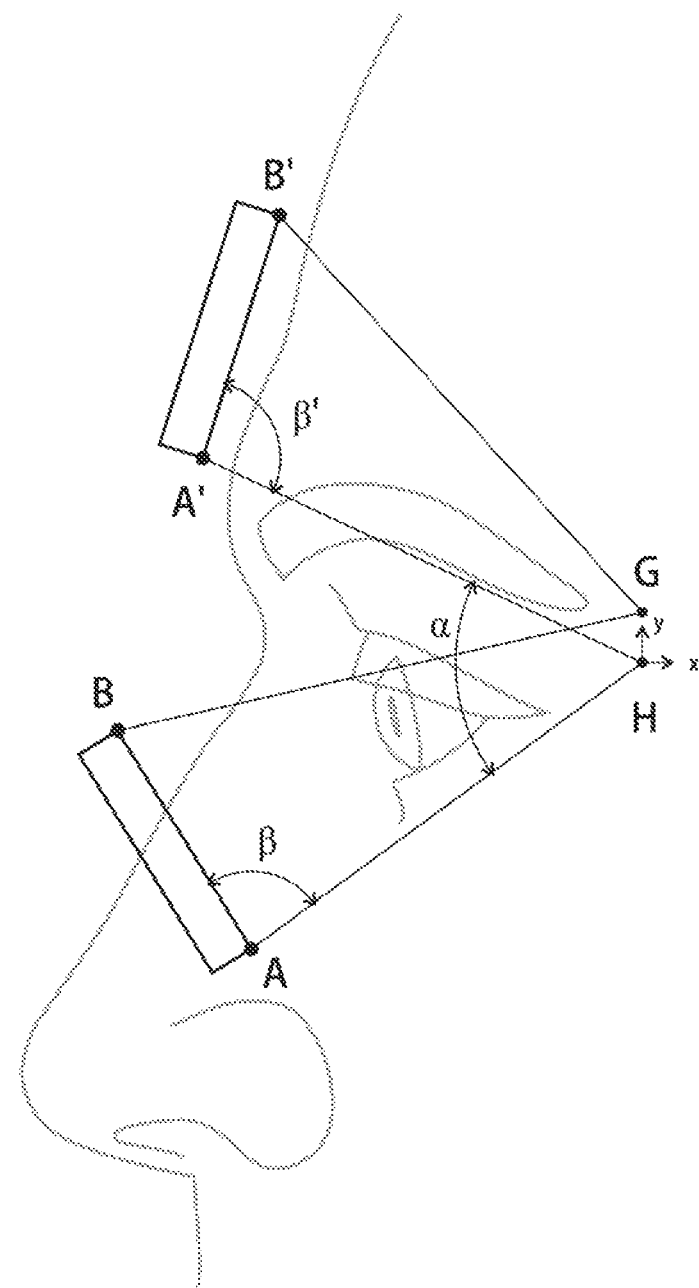
FIG. 16 shows an embodiment of a lever mechanism of rotary eyeglasses having four arms, according to the invention.

In view of the design problem (FIG. 16), length values of two elements (i.e., length of the follower link and the distance between the hinges) may be found based on length values of the other two elements (i.e., length of the guide link and length of the bar).

The above-stated analytical dependencies allow performing necessary calculations and developing a kinematic model of the design according to the following conditions:

distance between the eye pupil and the inner surface of the lens is between 15 mm and 25 mm, and the eyesight axis of the eye is inclined downward by 15 degrees relative to a horizontal line, when the user's head in a straight position;

a range of rotation of the movable frame is 70 to 85 degrees;

an angle of rotation of the movable frame about its longitudinal axis is equal to 413 upon lifting the movable frame.

Optimization of the design may be done by variation of the following values (taken in their projection to the sagittal plane):

length values of the beams (arms), while the hinges of the arms are secured to the fixed frame within area $C_1D_1E_1F_1$;

a distance between the distal hinges (i.e., the bar length), which is less than 20 mm;

an angle of rotation of the movable frame about its longitudinal axis ($\Delta\beta$), which is preferably in a range of 10 to 25 degrees.

Variation of the above values should be done while meeting the condition of securing proximal hinges of the arms to the fixed frame within area $C_1D_1E_1F_1$.

In view of basic ophthalmological parameters, size of conventional eyeglasses having foldable bows, and the above-indicated expressions, optimizing calculation may be performed for elements of the four-link lifting mechanism.

Figure 17:
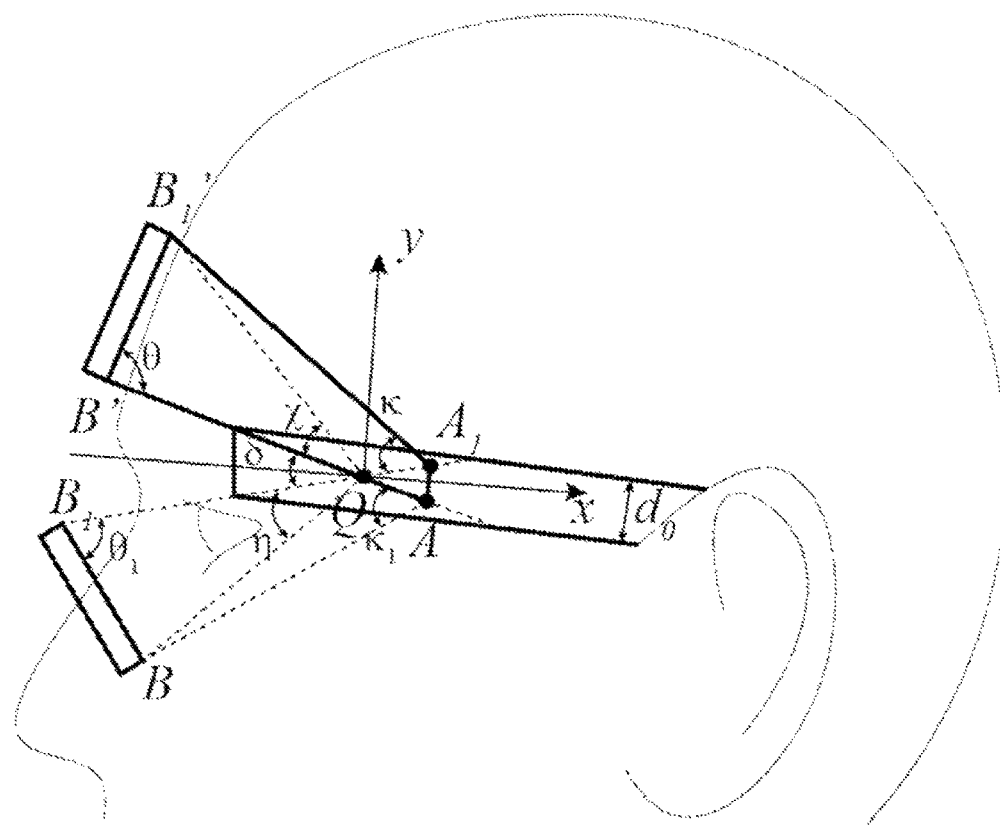
FIG. 17 illustrates a mathematical model for adjusting calculation of a four-link lever mechanism, according to the invention.

The Friedenstein method is further used for resolving four-link mechanism $AA_1B'B_1'$ (FIG. 17). Suppose that positions of the movable frame are already defined, i.e., length values QB=q, QB'=q', $QB_1=q_1$, $QB_1'=q_1'$, as well as angles $\delta$, $\chi$, $\eta$ are known. Suppose also that axis X coincides with the bisectrix of angle $\delta$ and is disposed in perpendicular to segment $AA_1$, and axis Y is disposed in perpendicular to axis X. By projecting the four-link mechanism $AA_1B'B_1'$ onto the axes and using Friedenstein method, the following expressions may be found:

$$AB' \cos(\delta/2) = B_1'A_1 \cos(\kappa - \delta/2) + B'B_1' \cos(\theta - \delta/2) \qquad (29)$$

$$AB' \sin(\delta/2) = B_1'A_1 \sin(\kappa - \delta/2) - B'B_1' \sin(0 - \delta/2) + AA_1 \qquad (30)$$

Suppose $AA_1 = a$, $BB_1 = B'B_1' = b$, where b is calculated as follows:

$$b = \sqrt{g_1'^2 - 2q'g_1'\cos\chi + q'^2} \qquad (31)$$

By moving terms not containing K from right portions of equations (29) and (30) to left portions, and by raising both equations to the second power and summing up thereof, the following first Friedenstein-like equation may be obtained for the four-link mechanism in position $AA_1B'B_1'$:

$$2bAB' \cos\theta + 2aAB' \sin(\delta/2) + 2ab \sin(\theta-\delta/2) = b^2 + a^2 - AB'^2 + A_1B_1'^2 \quad (32)$$

In the same way, the following second Friedenstein-like equation may be obtained for the four-link mechanism in position $AA_1BB_1$:

$$2bA_1B_1 \cos B_1 + 2aA_1B_1 \sin(\delta/2) + 2ab \sin(\theta_1-\delta/2) = b^2 + a^2 - AB^2 + A_1B_1^2 \quad (33)$$

By matching angles $\theta$ and $\theta_1$ with values defining positions of link $BB_1$ in triangles $BB_1Q$ and $B'B_1'Q$, the following expressions may be obtained:

$$\theta = \sin^{-1}\frac{b}{q_1'\sin\chi} \quad (34)$$

$$\theta_1 = \sin^{-1}\frac{b}{q\sin\eta} \quad (35)$$

By summing up expressions (32) and (33), the following expression may be obtained:

$$A_1B_1 + AB = \frac{b^2 + a^2 - ab(\sin(\theta_1 - \delta/2) + \sin(\theta - \delta/2))}{b(\cos\theta + \cos\theta_1) + 2a\sin(\delta/2)} \quad (36)$$

Total length of the links (arms) may be expressed in a form of a function of the length of link $AA_1$, i.e., $S_l(a) = A_1B_1 + AB$. Further, the optimization problem may be solved in the following two ways.

First way is optimization of the arm length. By finding minimum of function $S_l(a)$, when $$\frac{dS_l}{da} = 0,$$

the following expression may be obtained:

$$\frac{dS_l}{da} = \frac{ea^2 + a(2d - ec) - cd - eb^2}{(d + ae)^2} = 0 \quad (37)$$

where $$e = 2 \sin(\delta/2), c = b(\sin(\theta_1-\delta/2) + \sin(\theta-\delta/2)), d = b(\cos\theta + \cos\theta_1) \quad (38)$$

Further, an equation root corresponding to $S_{l\,min}$ may be obtained:

$$a_0 = (ec - 2d + \sqrt{(2d-ec)^2 + 4e(cd+eb^2)})/2e \quad (39)$$

Therefore, $S_{l\,min}$ value is:

$$S_{lmin} = \frac{b^2 + a_0^2 - ab(\sin(\theta_1 - \delta/2) + \sin(\theta - \delta/2))}{b(\cos\theta + \cos\theta_1) + 2a\sin(\delta/2)} \quad (40)$$

In the above-stated approach, optimization does not include minimization of the length of link $AA_1$, therefore, its length $a_0$ may considerably exceed size $d_0$ of the spectacle bow, which is undesirable. Thus, attention shall be paid to selection of point Q, which defines angle $\delta$. In this case the angle value may be obtained from the following equation:

$$a_0(\delta) = a_d \quad (41)$$

wherein at is maximal possible length of link $AA_1$ disposed on the bow. Further, the obtained angle value may be used in equation (40) and $S_{l\,min}$ value may be found.

After obtaining minimal total length of the links, the next link length may be found:

$$A_1B_1 = S_{l\,min} - AB \quad (42)$$

By substitution in equation (33) and excluding $A_1B_1$ therefrom, length of AB may also be found.

Based on initial data, it is found that optimal length of the arms (beams) for rotary eyeglasses is in a range of 20 mm to 60 mm, and the arm length depends on curvature of both fixed frame and movable frames. In other words, in designs where the movable frame has minimal curvature and the fixed frame has maximal curvature, the arm length is at a maximum; if the movable frame has maximal curvature of 8 units (i.e., when so-called "frame curvature angle" is 25 to 35 degrees), the arm length is at a minimum, especially when curvature of the fixed frame is not large.

A second way is optimization of the distance between the upper and lower proximal hinges; calculation is done in a similar manner and produces the optimal value of 20 mm or less.

The multi-lever mechanism that allows lifting the rotatable frame bearing the lenses and rotating the liftable frame about its longitudinal axis may be used in helmets (protective helmets or virtual reality helmets). The above-stated calculation methodology may be used for helmets also, with appropriate change in the initial data, according to the problem to be solved.

In some embodiments of the eyeglasses, the lenses, the movable frame and the fixed frame may be curved according to the head shape. Therefore, lengths of the arms (beams) of the lifting mechanism may be less than those calculated based on projections to the sagittal plane. However, this fact does not change the main principle of designing.

It shall be taken into account that due to specific features of the rotary eyeglasses of this invention, vertex distance of the eyeglasses may be somewhat greater than usual values, so positive optical power of the lenses needs to be decreased. Using aspheric or biaspheric lenses may also be advantageous.

When using four-link mechanism for lifting the movable frame, the hinges of the arms may be secured to the frame on opposite sides, so in some cases, even if the arms are crossed with the frame or with other arms in one projection, they would not interfere to each other, as they are disposed in different planes.

Figure 2:
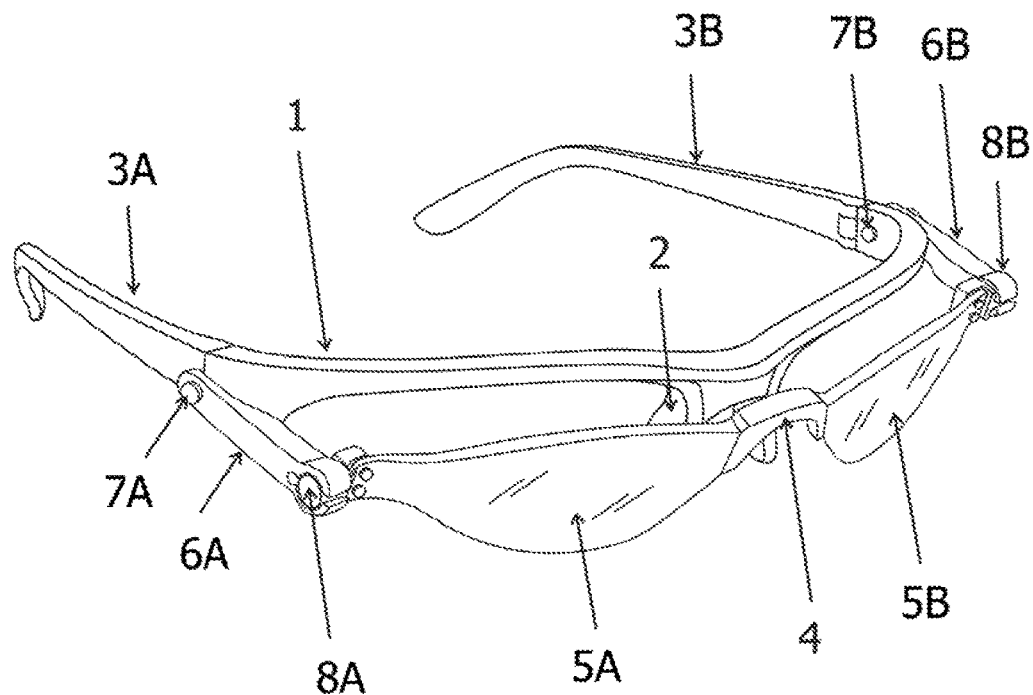
FIG. 2 shows a general view of rotary eyeglasses having two arms, according to the invention.

In some embodiments of the eyeglasses, the movable frame and/or the fixed frame may be U-shaped (FIG. 1).

Figure 5:
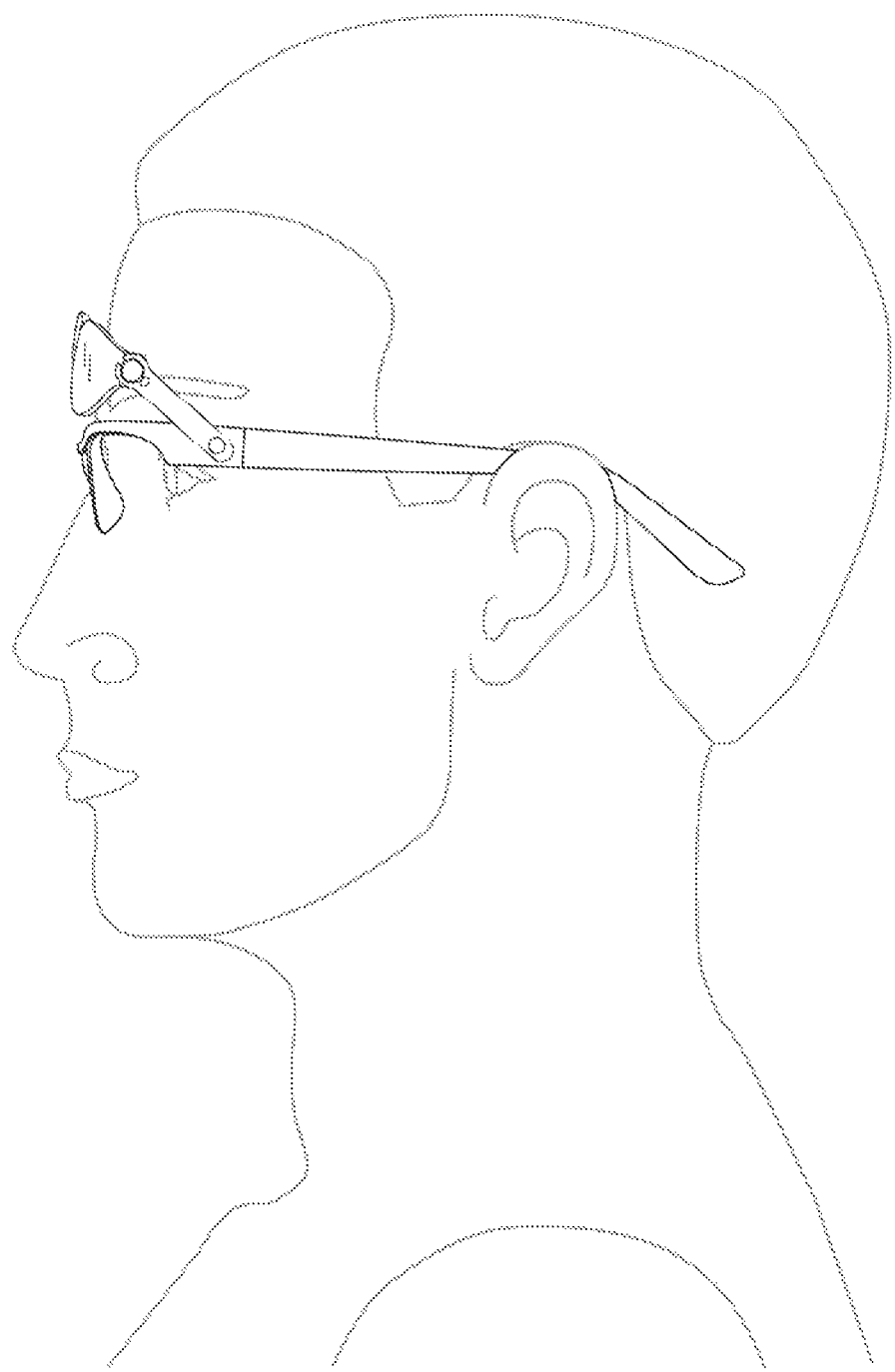
FIGS. 5 and 6 show rotary eyeglasses according to the invention in an uppermost position on a user.
Figure 6:
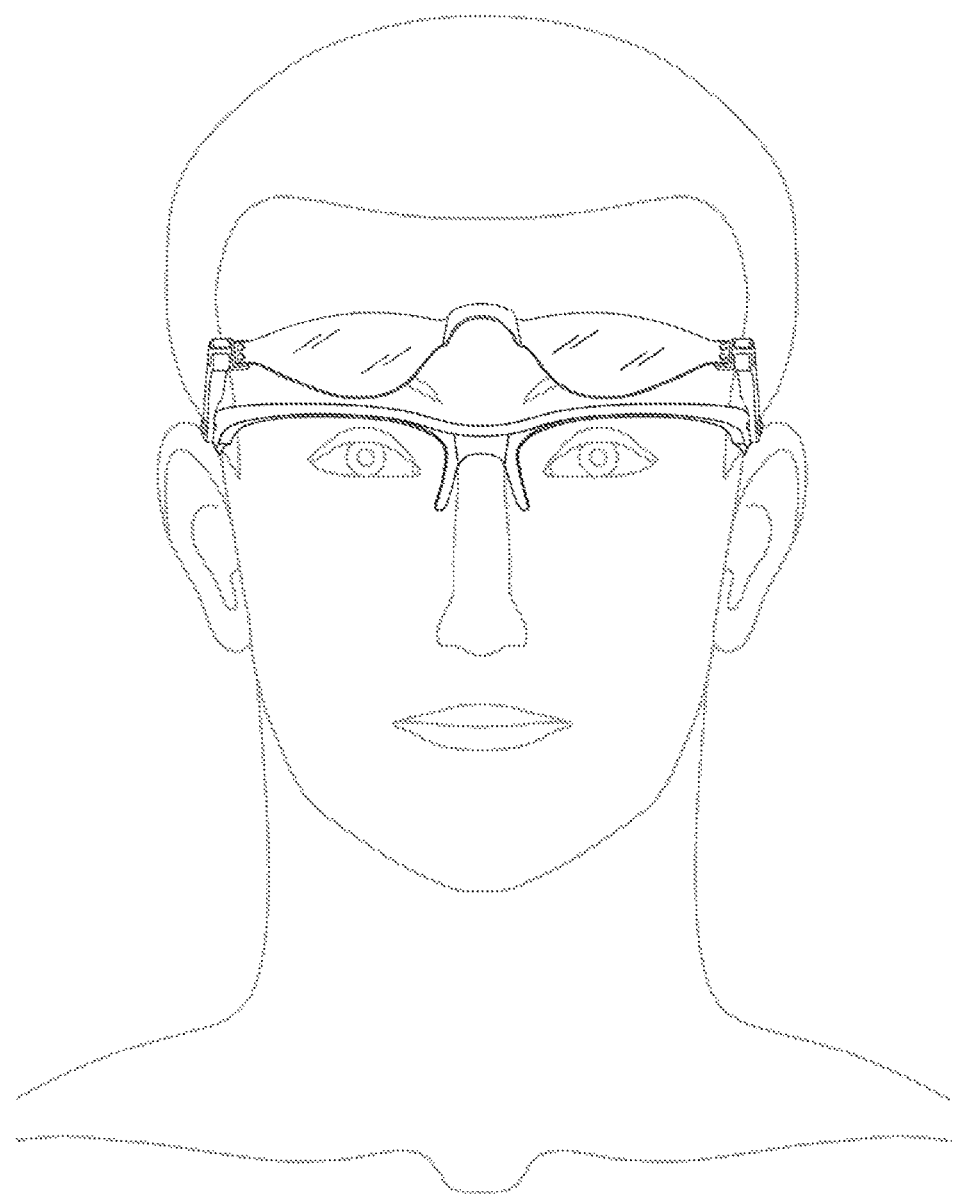
Figure 7:
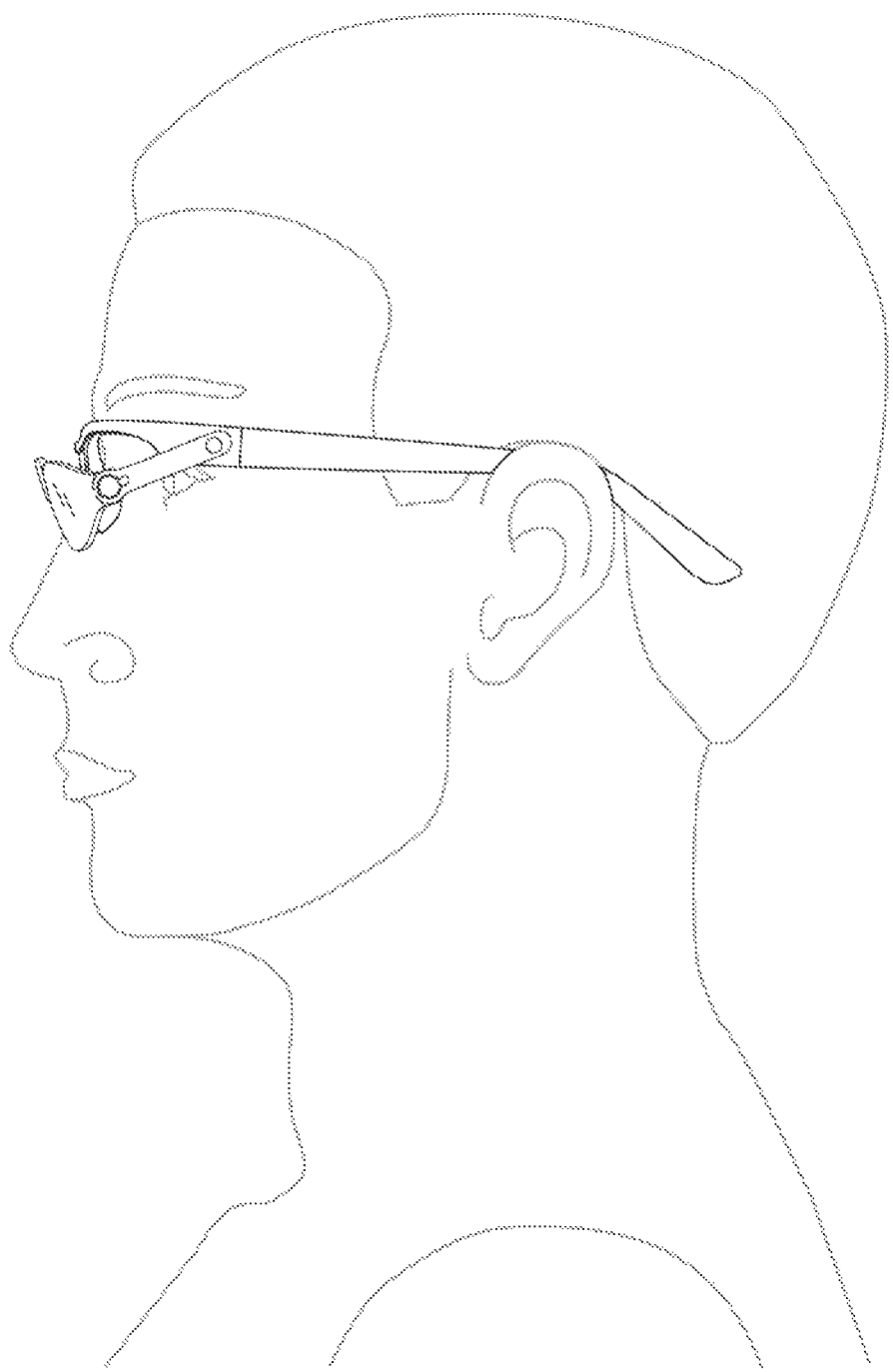
FIGS. 7 and 8 show rotary eyeglasses according to the invention in a middle position on a user.

In order to observe predetermined conditions, namely, a vertex distance and a pantoscopic angle, and also to avoid skewing the movable frame during its lifting, the longitudinal axis of the fixed frame passing through centers of proximal hinges preferably has to be positioned in parallel to the eye horizontal axis at a distance of 20 mm or less above the eye horizontal axis (FIGS. 5, 6, 7).

Rotation of the movable frame in a vertical plane (FIGS. 5, 6, 7) is provided about longitudinal axis of the fixed frame passing through centers of proximal hinges for securing the arms. Based on average statistical anthropometric data of a representative sample set including men and women over age 18, and taking into account usual shapes and sizes of conventional eyeglasses having foldable bows, the following conditions are preferable to be observed:

disposing proximal hinge for rotation of the movable frame so that the longitudinal axis of the fixed frame is positioned at a distance of 20 mm or less from the eye horizontal axis;

and disposing proximal hinges for rotation of the movable frame so that the longitudinal axis of the fixed frame is positioned above the eye horizontal axis.

In some embodiments, the rotary eyeglasses may additionally comprise a cam mechanism for changing rotation angle of the movable frame about its longitudinal axis, depending on angle of lifting the arms; they also may comprise means for locking up the movable frame in its uppermost and/or lowermost position.

Figure 18:
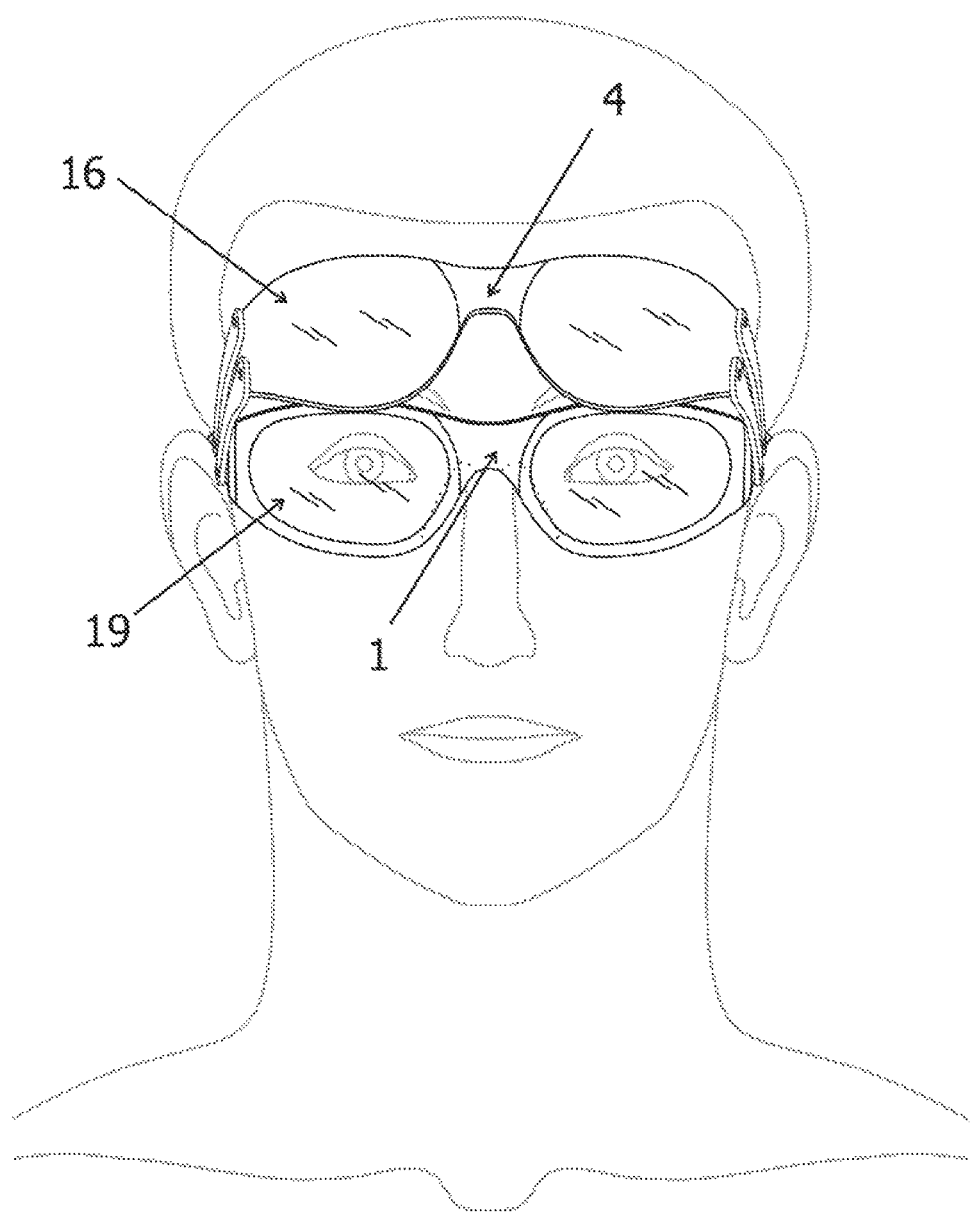
FIG. 18 shows an embodiment of rotary eyeglasses equipped with sunglasses, according to the invention.

The spectacle configuration allows using optical members of different types like lenses, protective glass elements, sunglasses elements, etc. An example of rotary eyeglasses having protective glasses or sunglasses 16 is shown in FIGS. 1 and 18.

Figure 20:
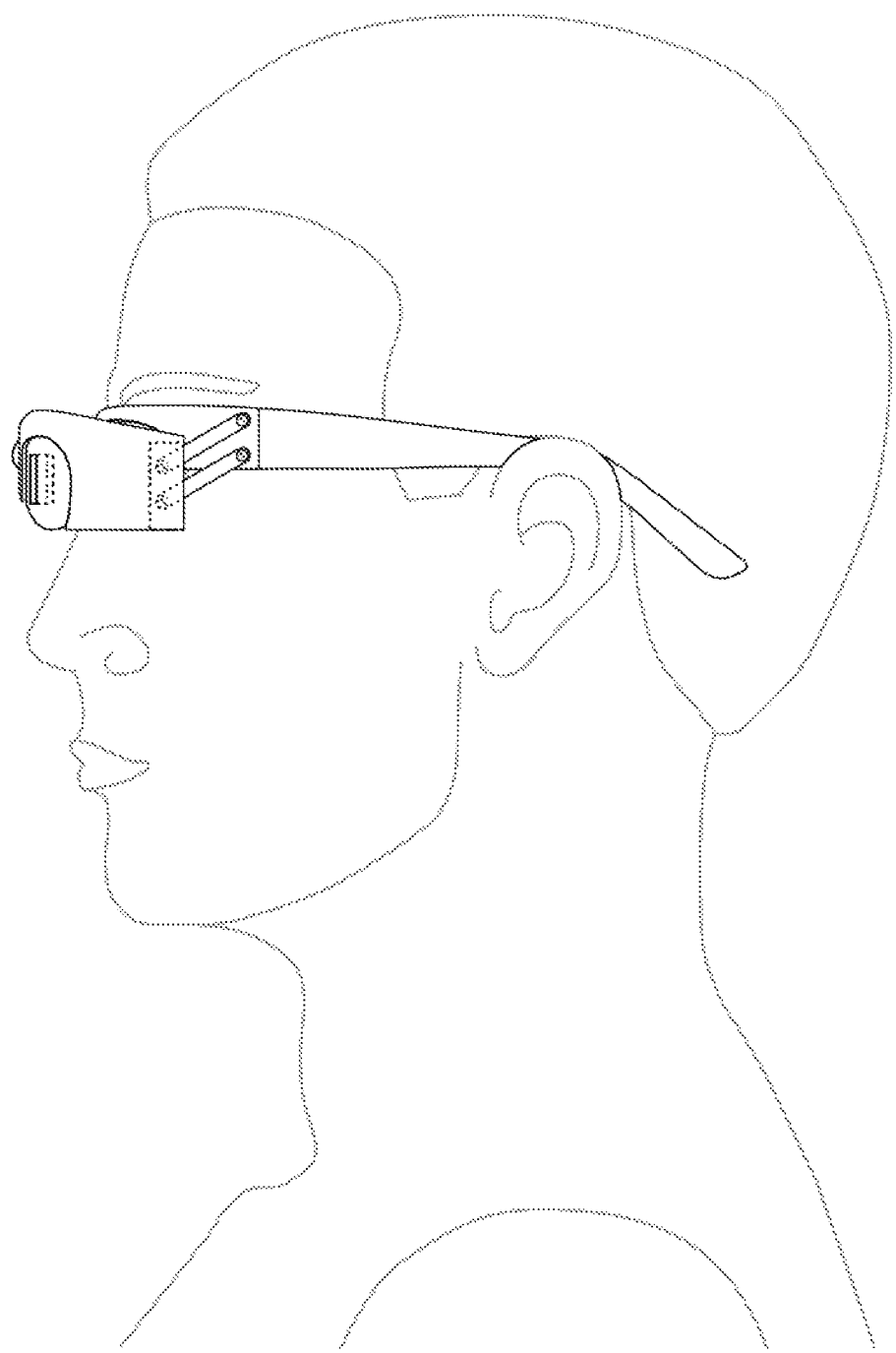
Figure 21:
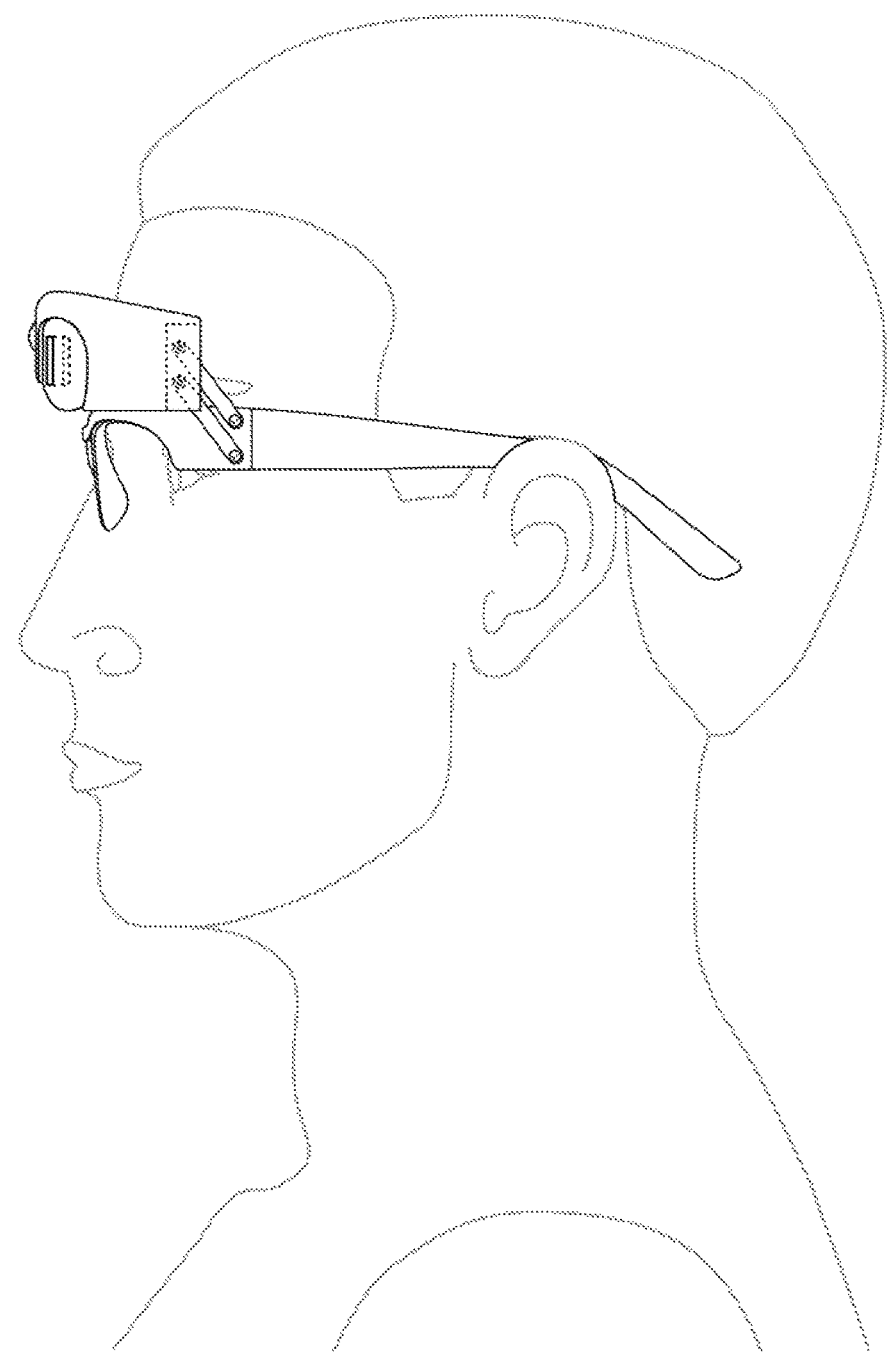
Figure 22:
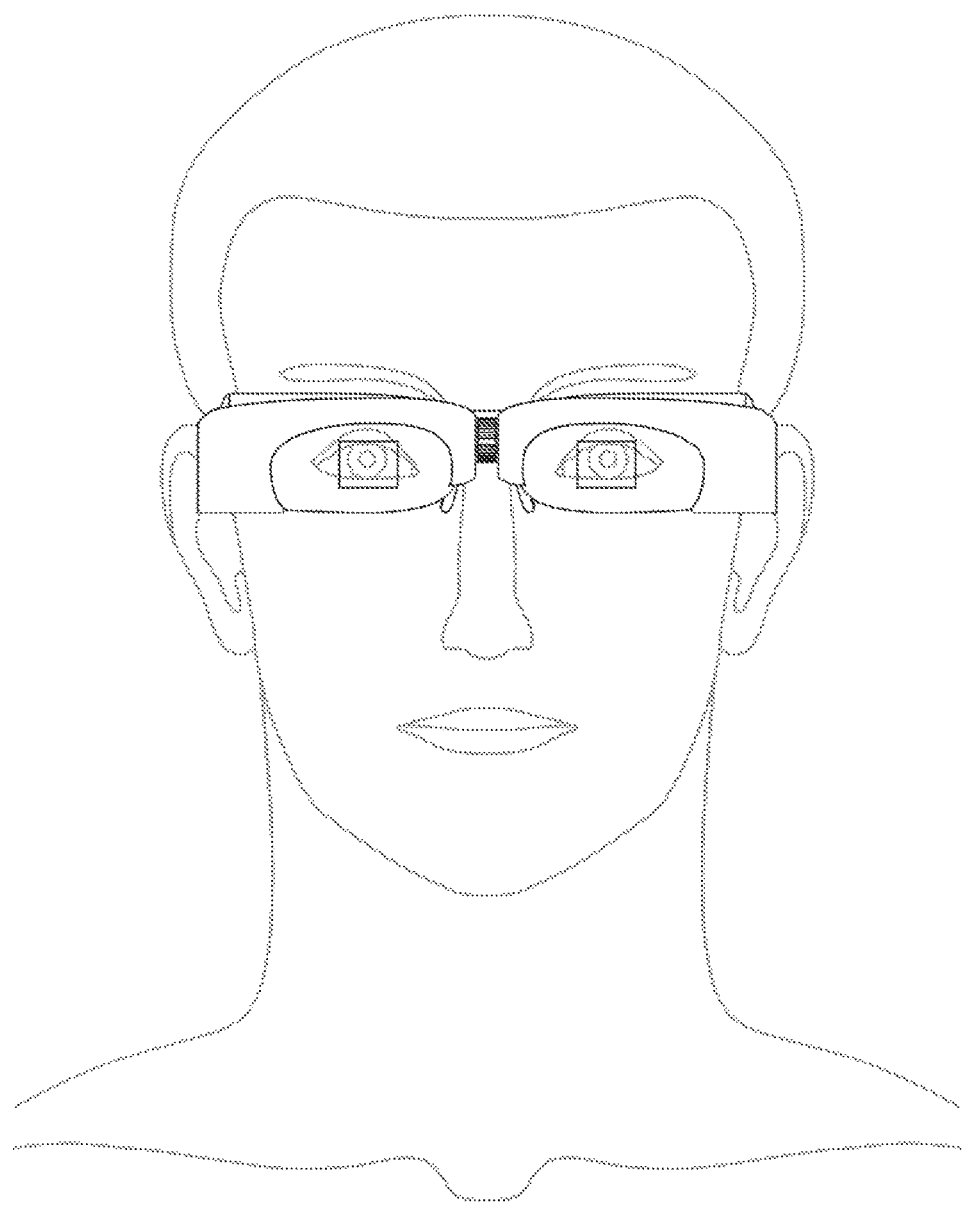

The invention may also be reduced into practice in a form of smart glasses (FIGS. 19, 20, 21, 22), where the optical members are displays 17A, 17B for displaying visual information to the user. In this case, three positions of the displays may be provided, a first position (FIG. 20) is when the movable frame is disposed in front of the user's eyes so that each display almost totally screens the vision field, like in virtual reality glasses; a second position is when the movable frame is moved up or down by 10 to 30 degrees relative to the first position so that each display partially screens the vision field never impeding straight look, like in augmented reality glasses, and the user may turn their eyes up or down and may see information represented on the displays; a third position is when the movable frame is moved up by more than 30 degrees (FIG. 21) so the user's vision field is almost unobstructed, as the movable frame with the displays disposed on it is located near the user's forehead.

Figure 19:
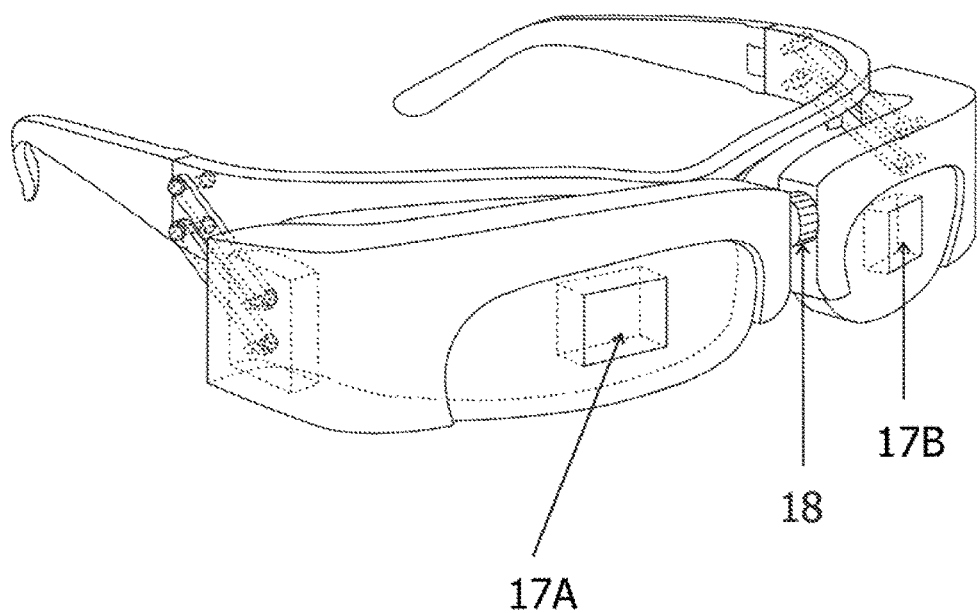
FIGS. 19, 20, 21, 22 show embodiments of rotary eyeglasses in a form of smart eyeglasses having two displays, according to the invention.

FIG. 19 shows eyeglasses with displays, wherein the movable frame provides possibility of adjustment of the distance between the displays, depending on the inter-pupil distance of the user. The nose arch of the movable frame is detachable and includes left and right threaded portions connected together by a nut 18. The user may rotate the nut to adjust the distance between the displays or other optical members according to their inter-pupil distance. In an alternative embodiment, adjustment of the distance between the optical members may be done by longitudinal sliding the optical members along the movable frame.

In some embodiments, the fixed frame includes optical members 19 located in front of the user's eyes (FIGS. 1, 18), and the movable frame comprises other optical members 16 like protective glass elements, sun glass elements, etc. This solution may be useful not only for people suffering from presbyopia, but also for people suffering from other eyesight disorders, e.g., myopia, who have to wear glasses constantly. With some types of eyesight disorder like astigmatism or combined presbyopia/myopia, when accommodation is blocked so the patient needs to use positive and negative lenses alternately, lenses may be mounted in both movable frame and fixed frame, wherein the fixed frame may be equipped with lenses available for constant use even when the movable frame is lifted up.

In some embodiments of the eyeglasses, two optical members mounted on a frame may be provided in a form of an integral member.

Figure 23:
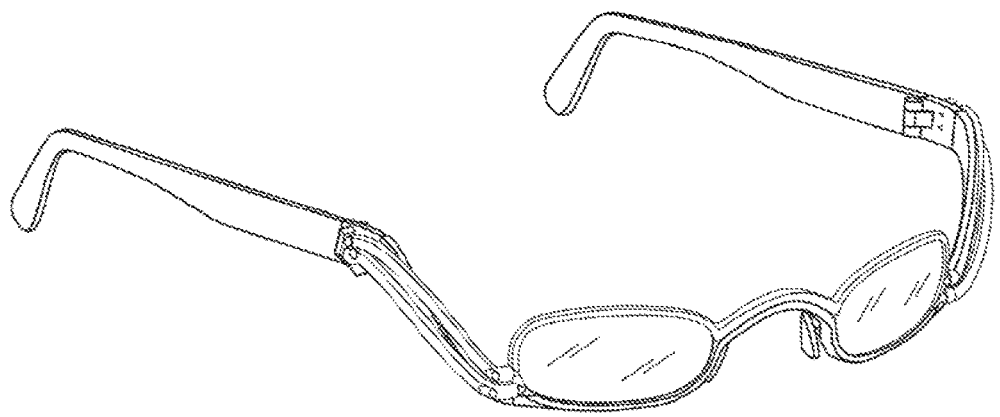
FIGS. 23, 24, 25 show preferred embodiments of rotary eyeglasses having four arms, according to the invention.
Figure 24:
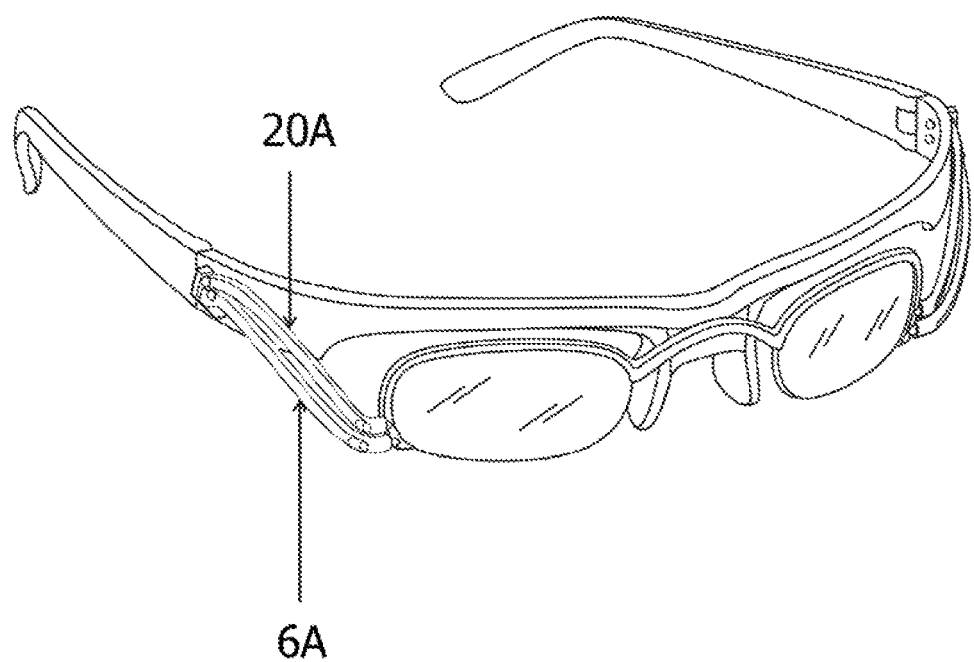

In some preferable embodiments (FIGS. 23, 24, 25), rotary eyeglasses contain a fixed frame with a nose abutment (nose pads) and two bows, a movable frame with optical members, and four arms (upper left arm, lower left arm, upper right arm, and lower right arm). Proximal ends of the right arms 20A and 6A are connected to the right lateral side of the fixed frame by corresponding hinges (the upper right arm 20A is connected by hinge 21), and proximal ends of the left arms are connected to the left lateral side of the fixed frame by corresponding hinges. The horizontal axis of rotation of the upper arms is substantially parallel to the horizontal axis of rotation of the lower arms. Distal ends of the left and right arms are connected to left and right lateral sides of the movable frame, respectively, by corresponding hinges (the upper right arm 20A is connected by hinge 23). The left and right arms and corresponding lateral sides of the fixed and movable frames form left and right four-link lever mechanisms configured to rotate the movable frame about its longitudinal axis.

Figure 25:
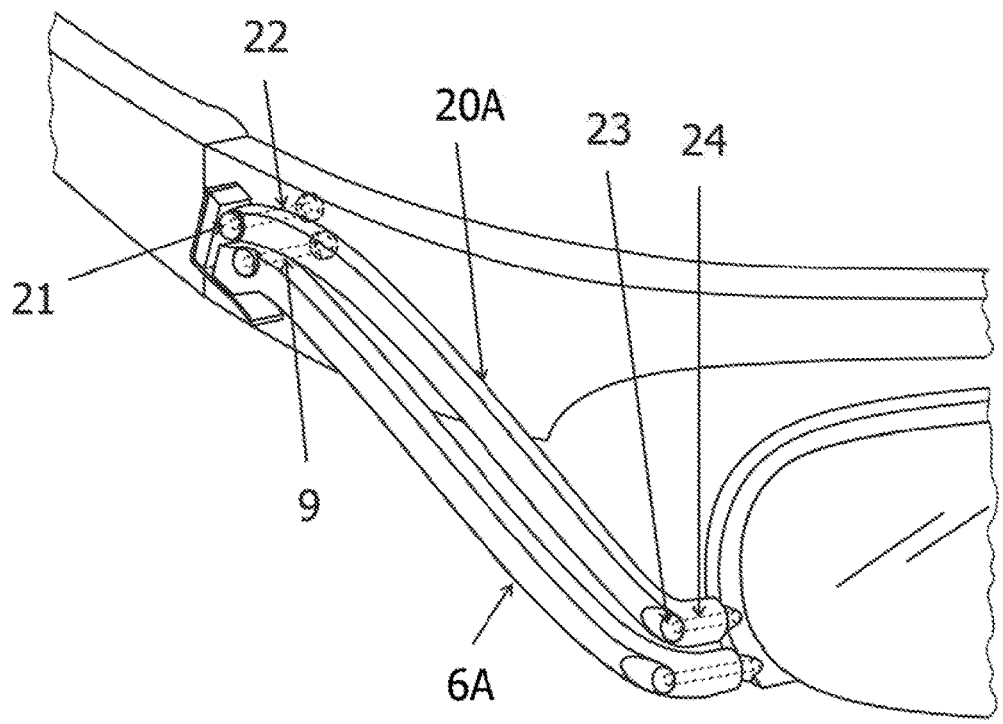

FIG. 25 shows an embodiment of the rotary eyeglasses having four-link lever mechanisms, wherein movability of the upper arms 20 in the hinges 21, 23 is ensured by pins 22, 24.

In some embodiments, additional arms may be configured to change distance between the distal and proximal hinges thereof in order to modify the pantoscopic angle. Moreover, the fixed frame and/or the movable frame may have additional connection points for the additional arms, which solution also allows modifying the pantoscopic angle.

In some embodiments, the rotary eyeglasses may additionally comprise a cord or a wire, which ends are connected to the proximal ends of the bows. Some embodiment of the rotary eyeglasses having displays may be used as a component of a wearable electronic system, and may be connected to another component of the system.

Figure 26:
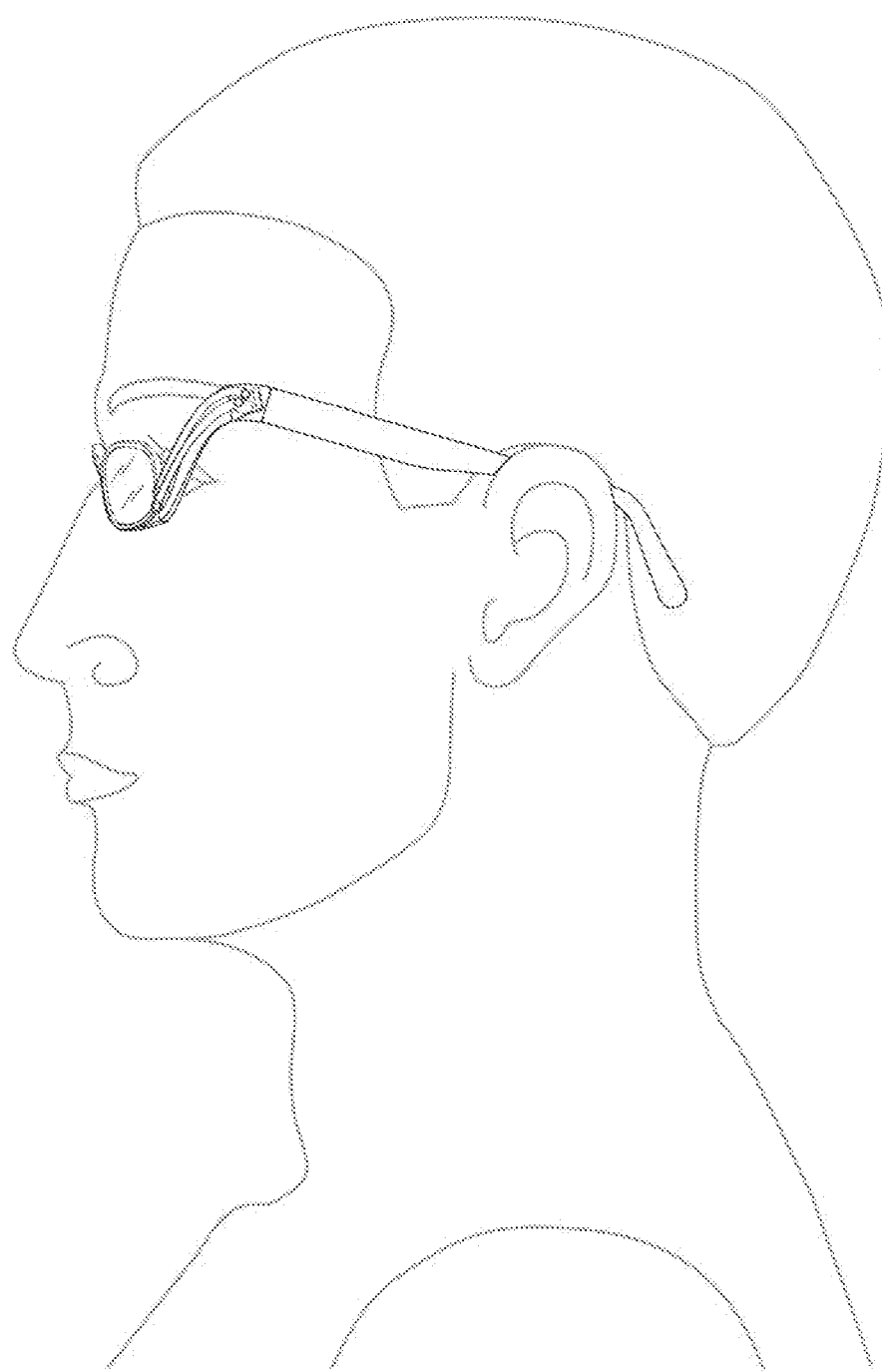
FIGS. 26, 27 show embodiments of rotary eyeglasses in which the fixed frame is located in a lower position on a user.
Figure 27:
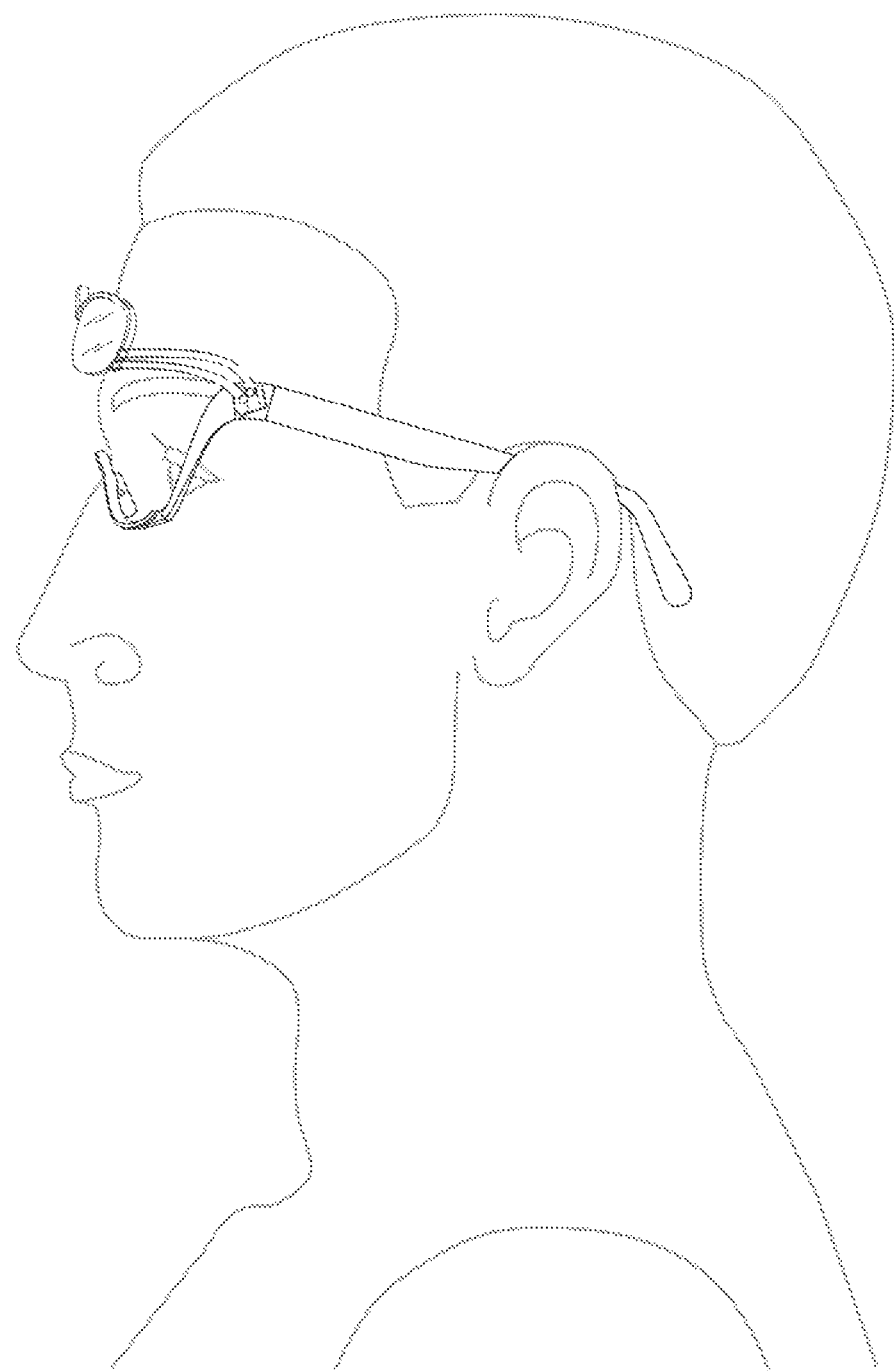
Figure 28:
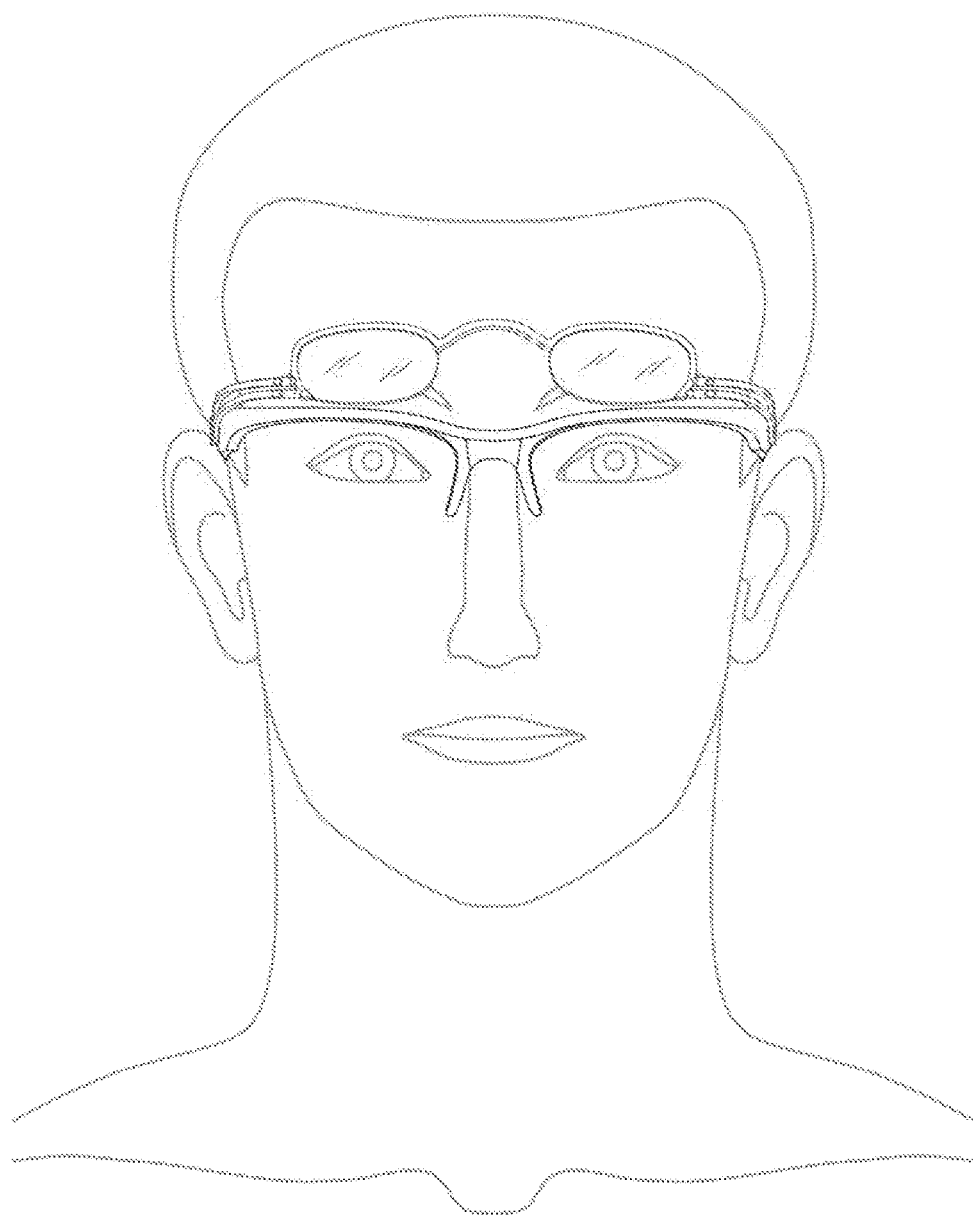
FIGS. 28, 29, 30, 31 show embodiments of rotary eyeglasses in which the fixed frame is located in an upper position on a user.
Figure 29:
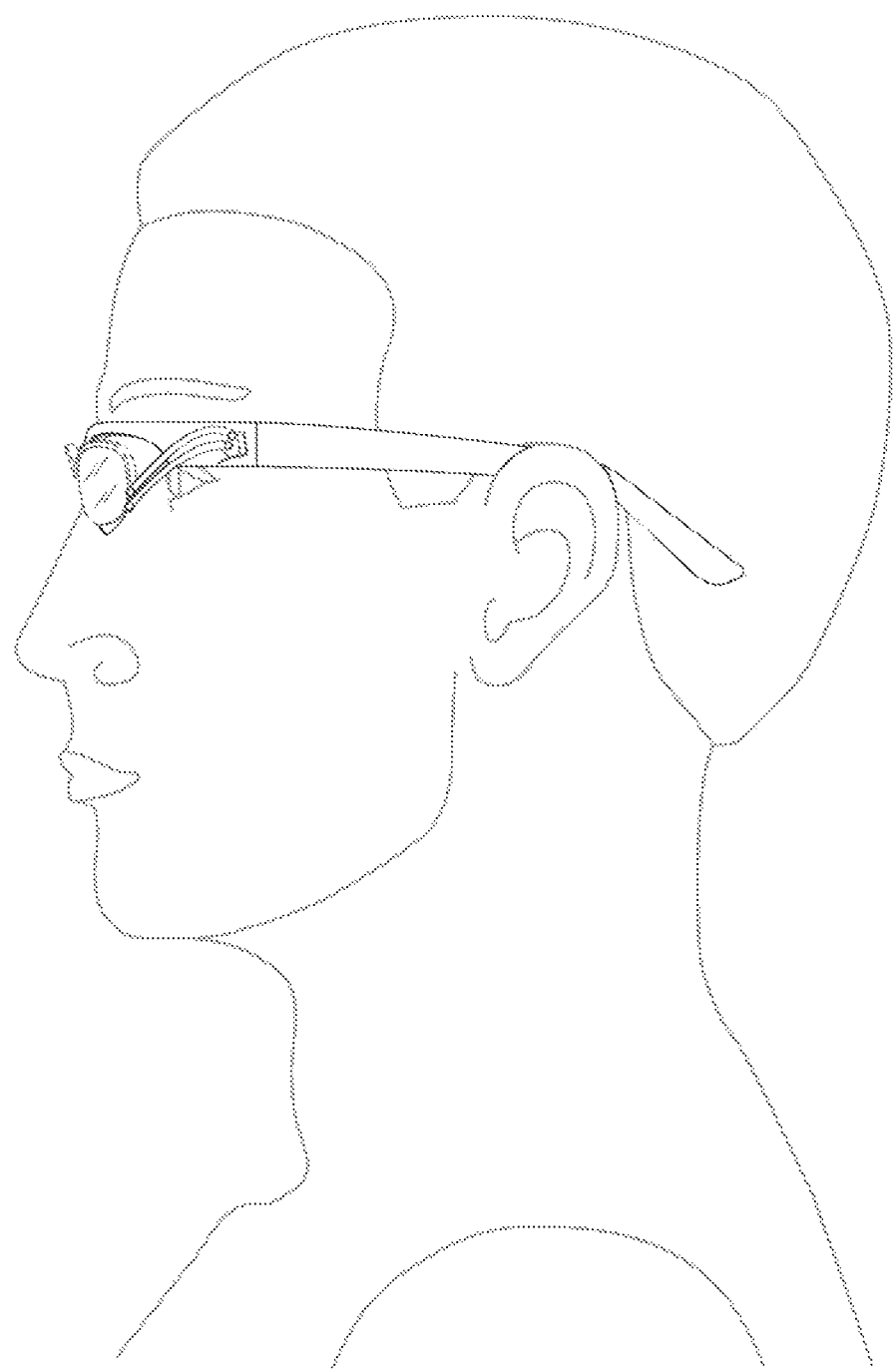
Figure 30:
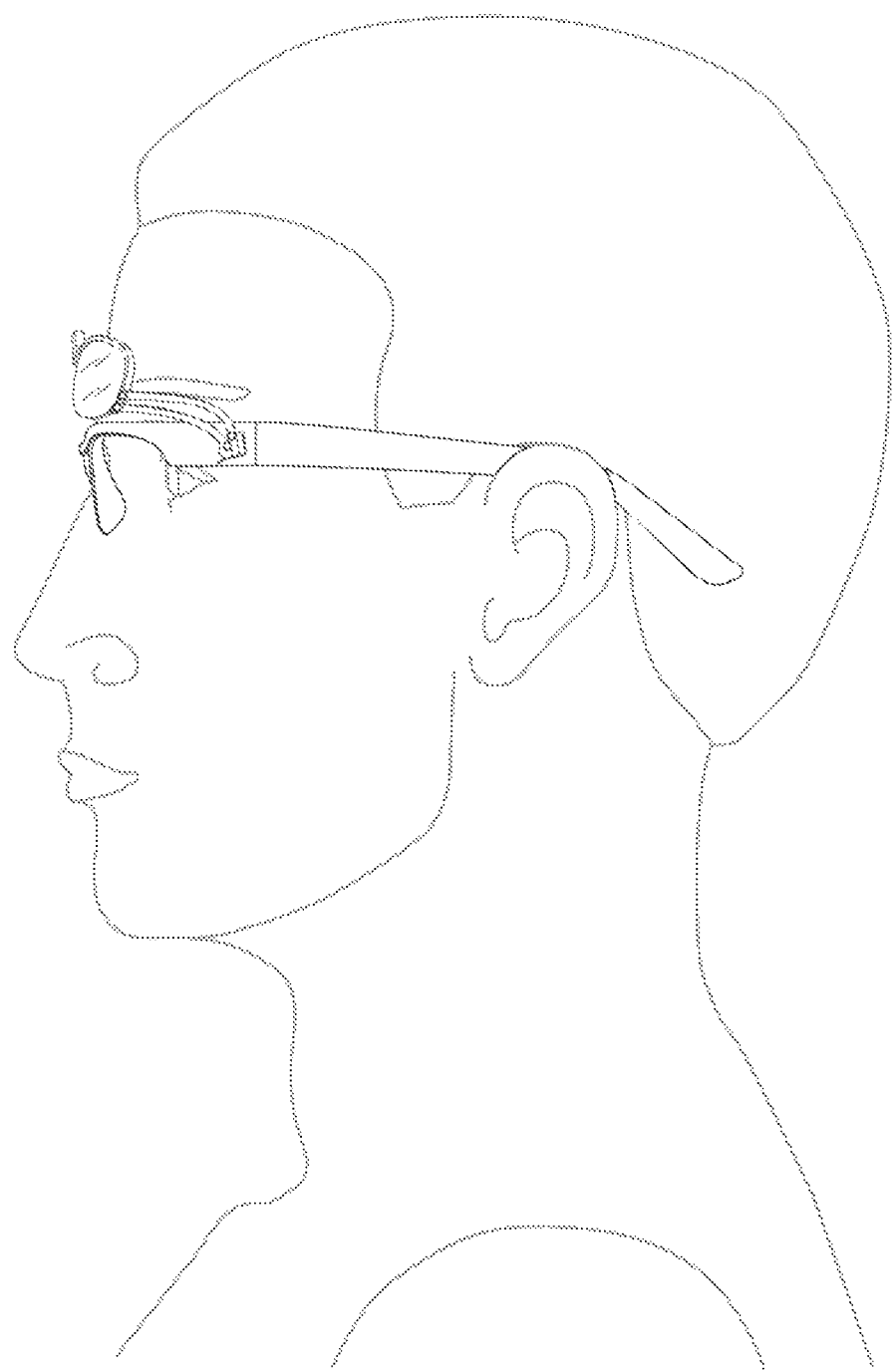
Figure 31:
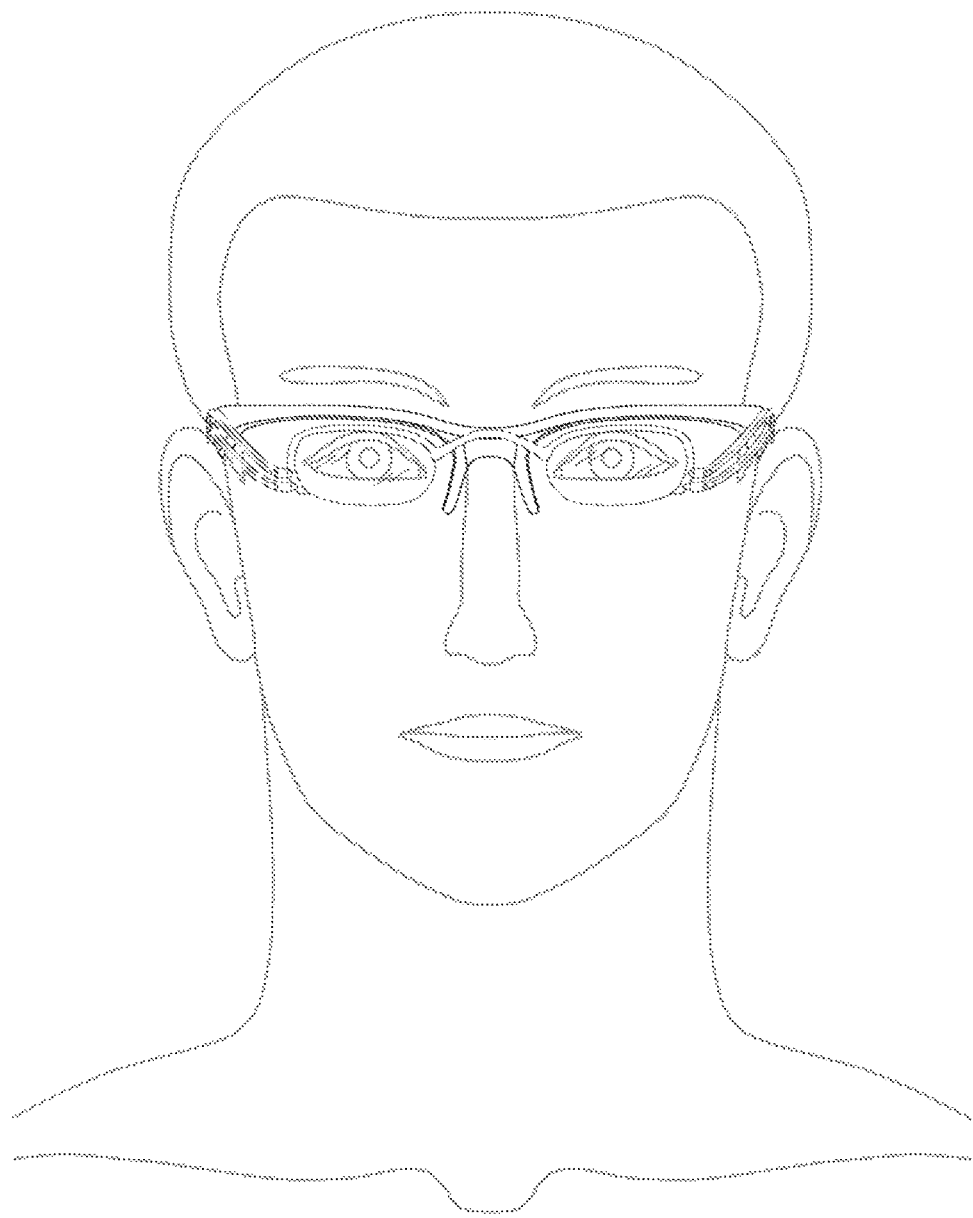

FIGS. 26, 27 show embodiments of the eyeglasses with lower disposition of the fixed frame.

In some embodiments, the fixed frame is positioned above the eye line when wearing the eyeglasses (FIGS. 28, 29, 30, 31).

Figure 32:
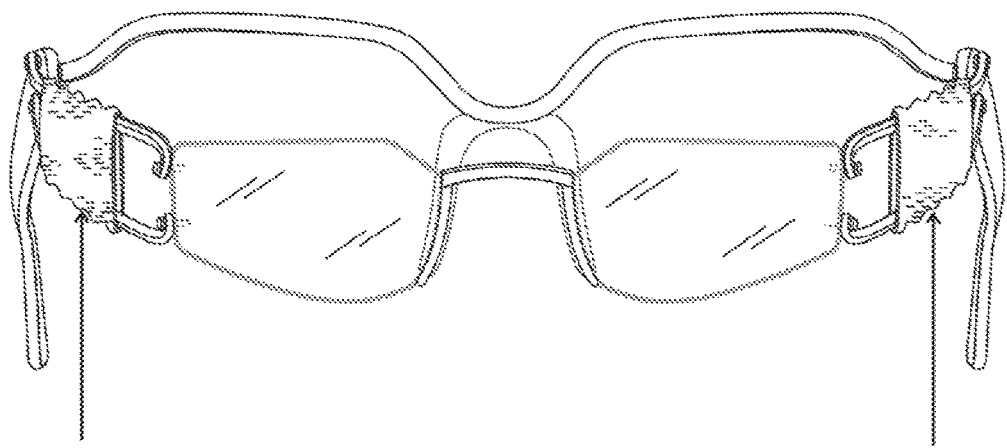
FIGS. 32, 33 show rotary eyeglasses with two sheaths.
Figure 33:
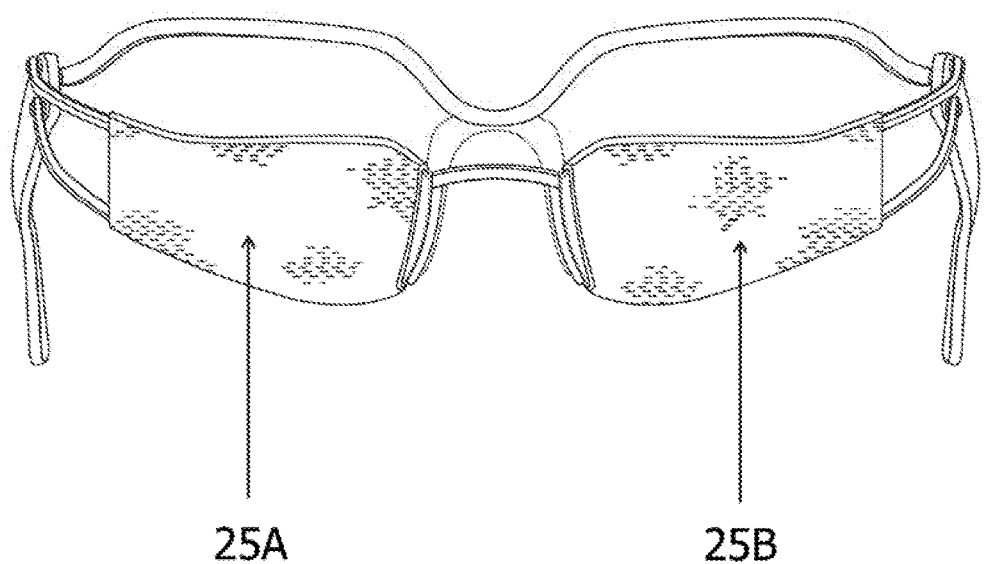

FIGS. 32, 33 show rotary eyeglasses additionally including two tubular elastic sheaths, a left sheath 25A and right sheath 25B, which are fixed on the left arm and the right arm, respectively, when the eyeglasses are in an operational position. The sheaths encompass optical members, when the eyeglasses are in a non-operational position in order to protect the optical members against damage and contamination.

If age-related presbyopia is not accompanied with another vision disorders like astigmatism or myopia, a user does not have to use eyeglasses constantly. Such a user does not need eyeglasses when driving a car or in similar circumstances. However, it is quite preferable that eyeglasses are always within reach, e.g., in a pocket. Using a rigid case for eyeglasses is not always convenient; taking eyeglasses out of the case and putting them back takes some time and complicates using the eyeglasses. In these cases it is expedient to use soft or elastic tubular sheaths, which constantly present on the eyeglasses both in operational and non-operational positions. When the eyeglasses are in an operational position, the sheaths are fixed on the rotatable arms between the corresponding lenses and bows, and when the eyeglasses are in a non-operational position, the sheaths cover the lenses. A flat or circular spring secured to the arm may be used on each of the left and right sides so as to stretch each sheath in vertical direction to make it substantially flat, when the eyeglasses are in an operational position.

Such springs allow fixing the sheaths on the lenses, when the eyeglasses are in a non-operational position in order to protect the lenses against damage and contamination.

Figure 34:
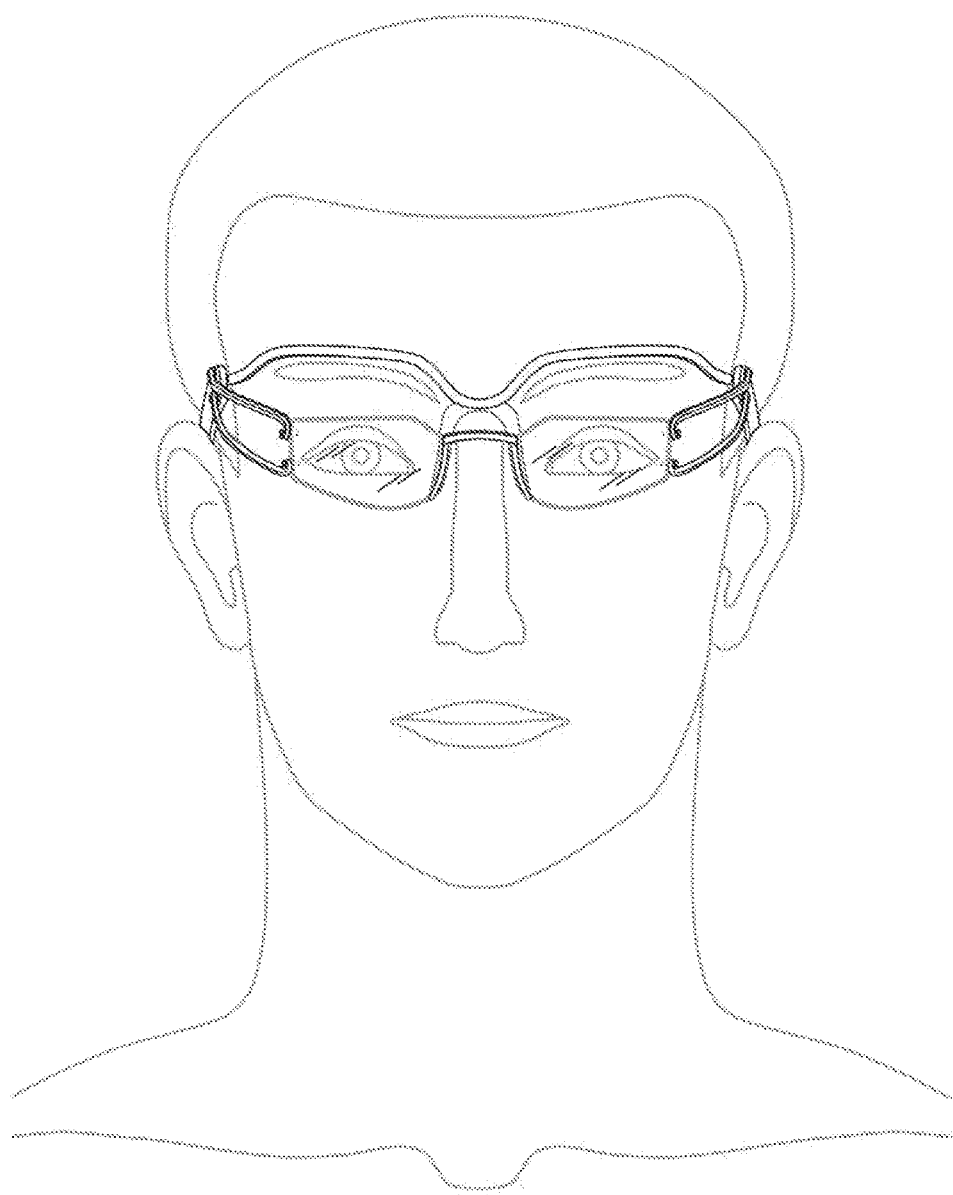
FIG. 34 shows another embodiment of design of rotary eyeglasses.

FIG. 34 shows another design option of the eyeglasses according to another embodiment the invention.

Having thus described the invention, it should be apparent to those skilled in the art that certain advantages of the described apparatus have been achieved.

It should also be appreciated that various modifications, adaptations, and alternative embodiments thereof may be made within the scope and spirit of the present invention. The invention is further defined by the following claims.

What is claimed is:

1. A rotary eyeglasses comprising:
   a fixed frame having left and right lateral ends;
   a nose abutment connected to the fixed frame at substantially equal distance from the lateral ends;
   right and left bows connected to the left and right lateral ends of the fixed frame, respectively;
   a movable frame having left and right lateral ends and comprising at least two optical members;
   left and right arms each having a distal end and a proximal end, wherein
   the proximal ends of the left and right arms are articulated to the left and right lateral ends of the fixed frame, respectively, and the distal ends of the left and right arms are articulated to the left and right lateral ends of the movable frame, respectively, so that the articulated joints provide rotation of the left and right arms substantially in parasagittal planes.

2. The eyeglasses of claim 1, wherein the points of the articulated joints between the arms and the lateral ends of the fixed frame are positioned at a vertical distance not greater than 20 mm from the horizontal eye axis.

3. The eyeglasses of claim 1, wherein the points of the articulated joints between the arms and the lateral ends of the fixed frame are positioned above the horizontal eye axis.

4. The eyeglasses of claim 1, further comprising at least one means for locking the movable frame in any position among multiple available positions.

5. The eyeglasses of claim 1, wherein the optical members are lenses.

6. The eyeglasses of claim 1, wherein the optical members are protective glass elements.

7. The eyeglasses of claim 1, wherein the optical members are electronic displays for displaying visual information to the user.

8. The eyeglasses of claim 1, wherein the movable frame is adjustable based on a distance between the pupils.

9. The eyeglasses of claim 1, wherein the fixed frame further comprises optical members in front of the user's eyes.

10. The eyeglasses of claim 1, further comprising left and right tubular sheaths, configured to encompass the left and right arms, respectively, when the eyeglasses are in an operational position; and
   configured to encompass the optical members, when the eyeglasses are in a non-operational position, in order to protect the optical members against damage and contamination.

11. A rotary eyeglasses comprising:
   a fixed frame having left and right lateral ends;
   a nose abutment connected to the fixed frame at substantially equal distance from the lateral ends;
   a movable frame having left and right lateral ends and comprising at least two optical members;
   upper left arm, lower left arm, upper right arm, and lower right arm, each having a distal and a proximal end, wherein
   the proximal ends of the upper and lower left arms and the upper and lower right arms are vertically spaced from each other and are articulated to the left and right lateral ends of the fixed frame, respectively, and
   the distal ends of the upper and lower left arms and the upper and lower right arms are vertically spaced from each other and are articulated to the left and right lateral ends of the movable frame, respectively, so that the upper and lower left arms and the upper and lower right arms and corresponding portions of the right and left lateral ends of the movable frame between the articulated joints and corresponding portions of the right and left lateral ends of the fixed frame between the articulated joints form four-link lever mechanisms substantially located in parasagittal planes of a user.

12. The eyeglasses of claim 11, wherein points of the articulated joints between the arms and the lateral ends of the movable frame at the left and right sides are located at a distance not greater than 20 mm.

13. The eyeglasses of claim 11, wherein an angle of rotation of the arms relative to the fixed frame is in a range of 10 to 25 degrees.

14. The eyeglasses of claim 11, wherein the optical members are optical lenses.

15. The eyeglasses of claim 11, wherein the optical members are protective glass elements.

16. The eyeglasses of claim 11, wherein the optical members are in electronic displays for displaying visual information to the user.

17. The eyeglasses of claim 11, wherein the movable frame is adjustable based on a distance between the pupils.

18. The eyeglasses of claim 11, wherein the fixed frame further comprises optical members disposed in front of a user's eyes.

19. The eyeglasses of claim 11, wherein the rotary eyeglasses further comprise a cord, whose ends are connected to the proximal ends of the bows.

20. The eyeglasses of claim 11, wherein the eyeglasses further comprise left and right tubular sheaths, configured so that the left and right sheaths encompass the upper and lower left arms and the upper and lower right arms, respectively, when the eyeglasses are in an operational position;
   the left and right sheaths encompass the optical members, when the eyeglasses are in a non-operational position in order to protect the optical members against damage and contamination.

21. The eyeglasses of claim 11, wherein the eyeglasses further comprise left and right tubular sheaths, configured so that the left and right sheaths encompass the left and right bows, respectively, when the eyeglasses are in an operational position;
   the left and right sheaths encompass the optical members, when the eyeglasses are in a non-operational position, in order to protect the optical members against damage and contamination.

* * * * *